(12) United States Patent
Ryu et al.

(10) Patent No.: US 9,408,910 B2
(45) Date of Patent: Aug. 9, 2016

(54) ANTICANCER PRODRUG ACTIVATED BY RADIATION OR ULTRAVIOLET TREATMENT AND USE THEREOF

(75) Inventors: Ju-Hee Ryu, Seoul (KR); Kwang-Meyung Kim, Seoul (KR); Ick-Chan Kwon, Seoul (KR); Kui-Won Choi, Seoul (KR); Sang-Yoon Kim, Seoul (KR); Beom-Suk Lee, Seoul (KR); Dae-Yoon Chi, Seoul (KR); Hee-Seup Kil, Seoul (KR); Hyun-Ju Sung, Seoul (KR)

(73) Assignee: KOREA INSTITUTE OF SCIENCE AND TECHNOLOGY, Seoul (KR)

( * ) Notice: Subject to any disclaimer, the term of this patent is extended or adjusted under 35 U.S.C. 154(b) by 0 days.

(21) Appl. No.: 14/001,745

(22) PCT Filed: Mar. 2, 2011

(86) PCT No.: PCT/KR2011/001438
§ 371 (c)(1),
(2), (4) Date: Aug. 27, 2013

(87) PCT Pub. No.: WO2012/118237
PCT Pub. Date: Sep. 7, 2012

(65) Prior Publication Data
US 2013/0338422 A1 Dec. 19, 2013

(51) Int. Cl.
*A61K 41/00* (2006.01)
*A61N 5/06* (2006.01)
*A61N 5/10* (2006.01)
*A61K 47/48* (2006.01)
*A61K 31/704* (2006.01)
*A61K 38/00* (2006.01)

(52) U.S. Cl.
CPC ............ *A61K 41/0042* (2013.01); *A61K 31/704* (2013.01); *A61K 47/48246* (2013.01); *A61N 5/062* (2013.01); *A61N 5/1001* (2013.01); *A61K 38/00* (2013.01)

(58) Field of Classification Search
None
See application file for complete search history.

(56) References Cited

U.S. PATENT DOCUMENTS

| | | | |
|---|---|---|---|
| 2004/0052793 A1* | 3/2004 | Carter | A61K 47/48246 424/146.1 |
| 2007/0104719 A1 | 5/2007 | Carter et al. | |
| 2008/0193431 A1* | 8/2008 | Zheng | A61K 47/48053 424/94.1 |

OTHER PUBLICATIONS

Kyu-Chul, Kim, "Development of a prodrug activated by caspase-3," www.riss.kr/link?id=T11929818, uploaded Feb 2010, Abstract.*
Law, Benedict et al. "Proteolysis: A Biological Process Adapted in Drug Delivery, Therapy, and Imaging." *Bioconjugate Chemistry* vol. 20, No. 9, Sep. 2009, pp. 1683-1695.
Stefflova, Klara et al. "Targeted Photodynamic Therapy Agent with a Built-In Apoptosis Sensor for in Vivo Near-Infrared Imaging of Tumor Apoptosis Triggered by Its Photosensitization in Situ." *Molecular imaging* vol. 5, No. 4, 2006, pp. 520-532.
Rai, Prakash, et al. "Development and applications of photo-triggered theranostic agents." *Advanced Drug Delivery Rreviews* vol. 62, 2010, pp. 1094-1124.
Wojtyk, James TC, et al. "Exploiting tumour biology to develop novel drug delivery strategies for PDT." *Medical Laser Application*, vol. 21, 2006, pp. 225-238.
Kim, Sungwon, et al. "Engineered polymers for advanced drug delivery." *European Journal of Pharmaceutics and Biopharmaceutics* vol. 71, 2009, pp. 420-430.
Tamm, Ingo, et al. "IAP-Family Protein Survivin Inhibits Caspase Activity and Apoptosis Induced by Fas (CD95), Bax, Caspases, and Anticancer Drugs." *Cancer Research*, vol. 58, 1998, pp. 5315-5320.
International Search Report mailed Dec. 21, 2011 in corresponding International Application No. PCT/KR2011/001438.
Kyu-Chul Kim, "Development of a prodrug activated by capase-3," www.riss.kr/link?id=T11929818, uploaded Feb. 2010, Abstract.

* cited by examiner

*Primary Examiner* — Amber D Steele
*Assistant Examiner* — Schuyler Milton
(74) *Attorney, Agent, or Firm* — Foley & Lardner LLP

(57) ABSTRACT

The present invention relates to an anticancer prodrug consisting of peptide of acetyl-SEQ ID NO: 1-linker-anticancer drug. The anticancer prodrug effectively provides an anticancer drug unstable in acid or base, such as doxorubicin, in a form of prodrug. Thus, the anticancer prodrug exists as a non-toxic inactive form when administered into the body, but effectively releases the anticancer drug as an active ingredient in the target area in the presence of caspase activated by radiation or UV treatment after administered into the body. Accordingly, the anticancer drug exhibits selective anticancer effects on cancer cells, thereby maximizing the therapeutic effect and minimizing the side-effects of chemotherapy.

7 Claims, 27 Drawing Sheets
(20 of 27 Drawing Sheet(s) Filed in Color)

Fig. 1
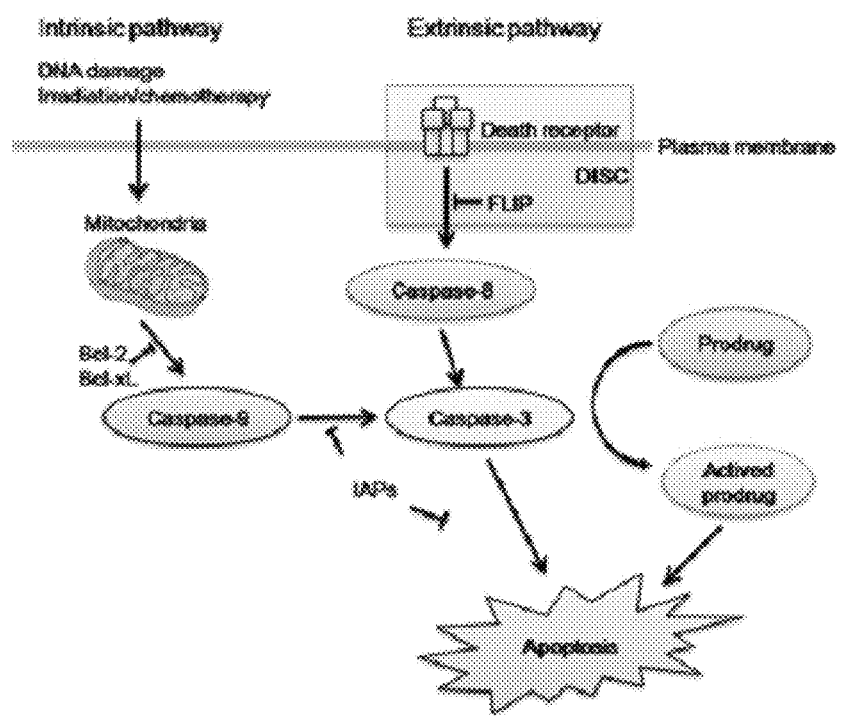
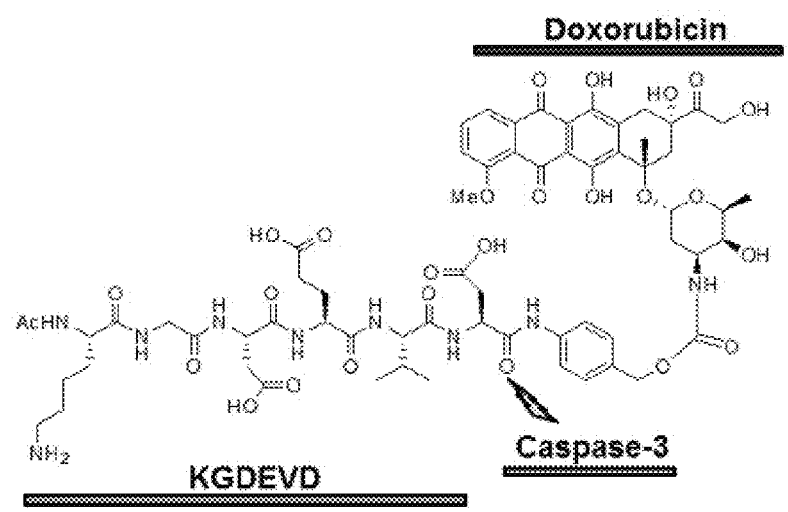

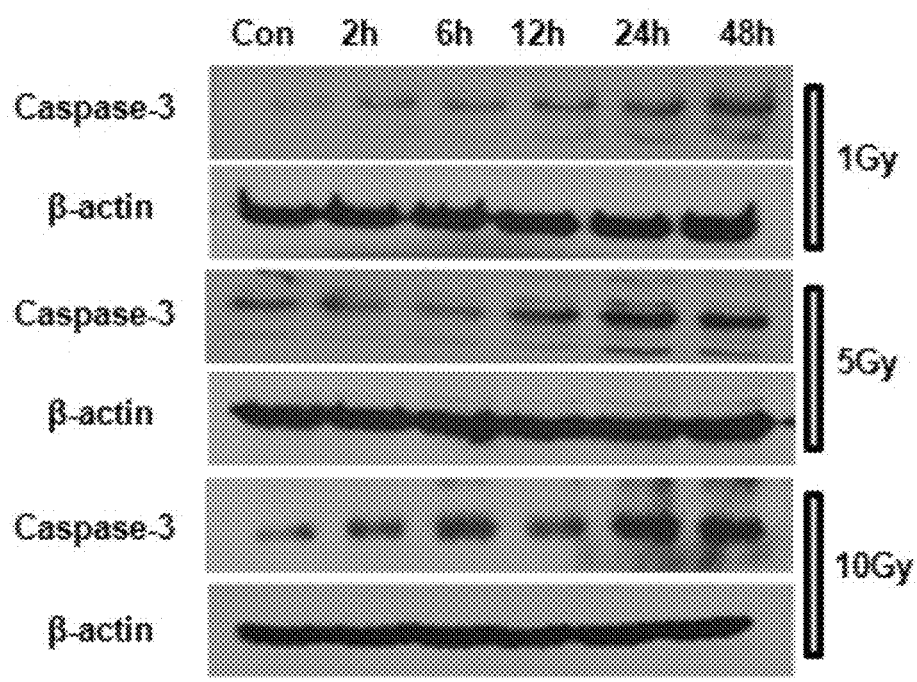

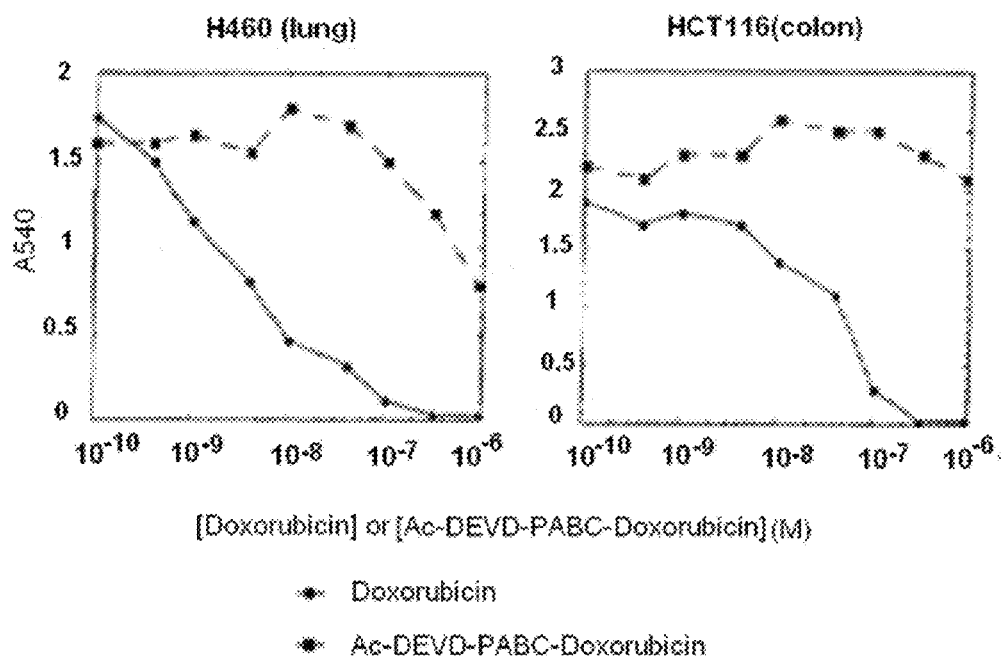

Fig. 12
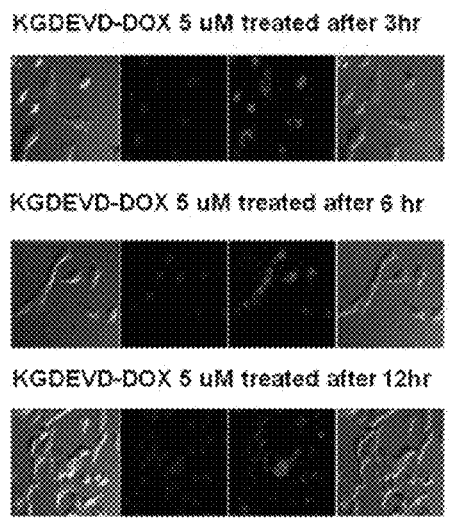
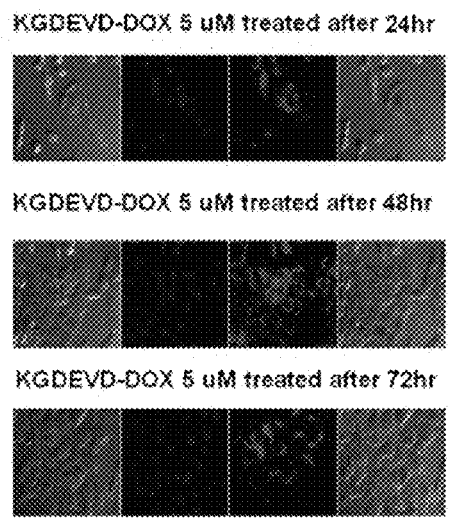

Fig. 14
KGDEVD-DOX 5uM treated after 24hr
and 5Gy Irradiation after 3hr
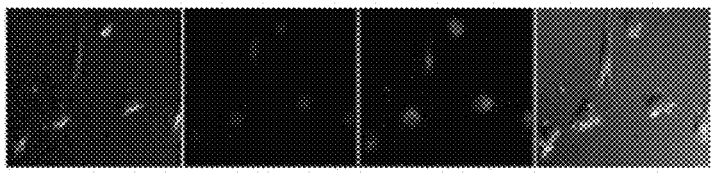
KGDEVD-DOX 5uM treated after 24hr
and 5Gy Irradiation after 6hr
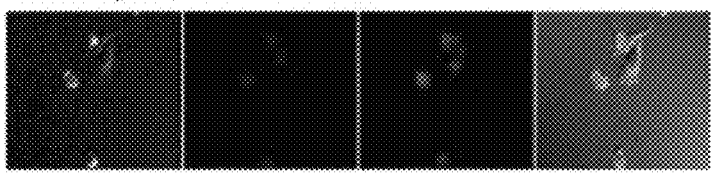
KGDEVD-DOX 5uM treated after 24hr
and 5Gy Irradiation after 12hr
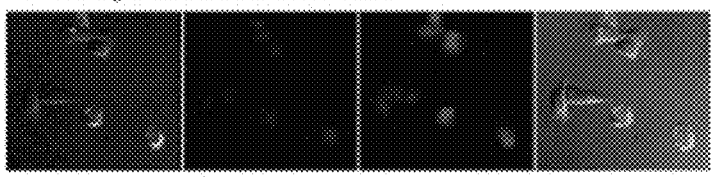
KGDEVD-DOX 5uM treated after 24hr
and 5Gy Irradiation after 24hr
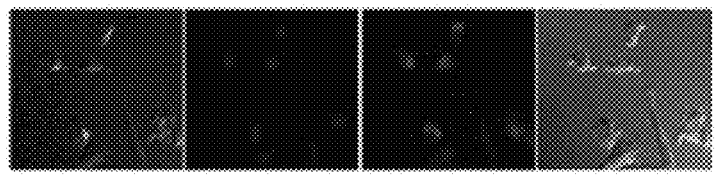
KGDEVD-DOX 5uM treated after 24hr
and 5Gy Irradiation after 48hr
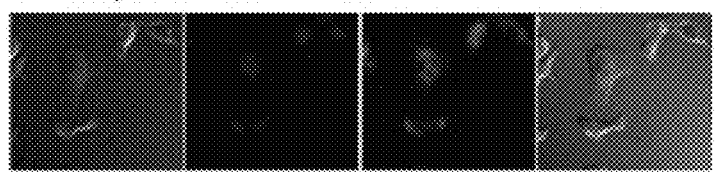
KGDEVD-DOX 5uM treated after 24hr
and 5Gy Irradiation after 72hr
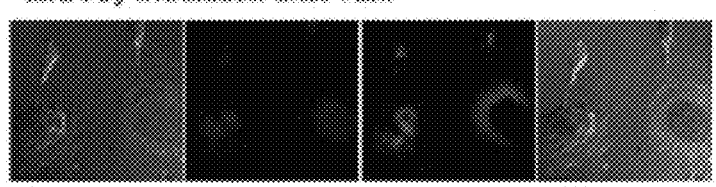

Fig. 15
KGDEVD-DOX 5uM treated after 24hr + Ultraviolet none treated
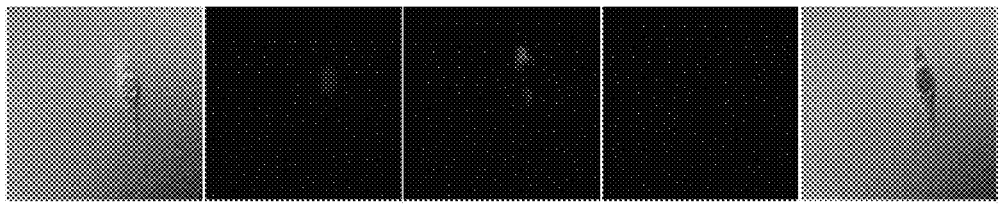
KGDEVD-DOX 5uM treated after 24hr + Ultraviolet treated after 3hr
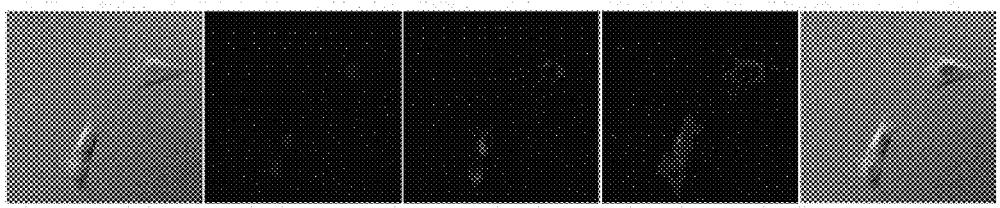
KGDEVD-DOX 5uM treated after 24hr + Ultraviolet treated after 6hr
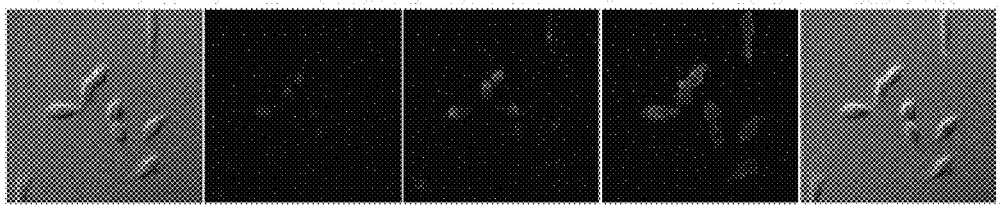
KGDEVD-DOX 5uM treated after 24hr + Ultraviolet treated after 12hr
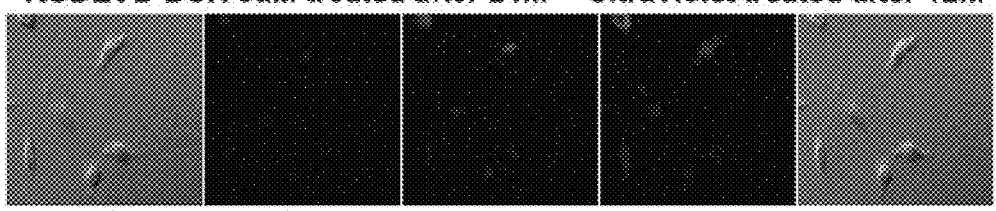
KGDEVD-DOX 5uM treated after 24hr + Ultraviolet treated after 24hr
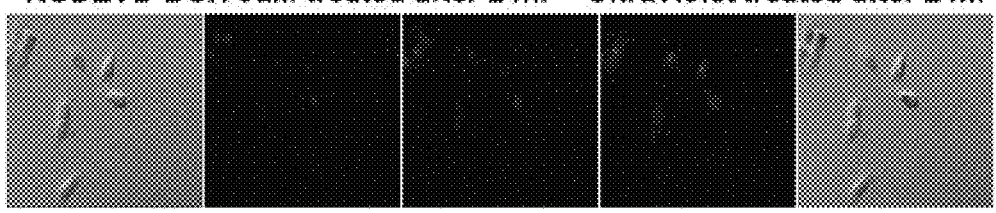

ANTICANCER PRODRUG ACTIVATED BY RADIATION OR ULTRAVIOLET TREATMENT AND USE THEREOF

CROSS-REFERENCE TO RELATED APPLICATIONS

This application is a U.S. national stage application of PCT/KR2011/001438 filed Mar. 2, 2011 the content of which is incorporated herein by reference.

BACKGROUND OF THE INVENTION

1. Field of the Invention

The present invention relates to an anticancer prodrug capable of releasing an anticancer drug as an active ingredient, which is cleaved by caspase activated in vivo by radiation of radioactive ray or UV, a preparation method thereof, and use thereof.

2. Description of the Related Art

Now, cancer is a disease that ranks as the first leading cause of death in Korea, and the number of cancer patients will grow due to environmental factors, increasing life expectancy, western dietary patterns or the like. The most common cancer treatment is radiotherapy in conjunction with the conventional chemotherapy.

Many forms of chemotherapy and radiotherapy are based on the principle of treating cancer by induction of cancer cell apoptosis. Further, the therapeutic effect can be more enhanced by using radiotherapy in conjunction with anticancer drugs used in the conventional chemotherapy.

However, although the conventional chemotherapy and radiotherapy are excellent in inhibition of cancer cell growth and apoptosis, high doses of anticancer drugs or radiation are toxic to normal cells as well as to cancer cells, which causes severe side effects.

Therefore, targeted therapies have been recently developed, and they are new promising treatment options that have a different mechanism from the conventional chemotherapy or hormone therapy. Targeted therapies do not act on normal cells, but target cell signaling pathways involved in tumor growth, and receptor and genetic mutations, and thus they are the best anticancer drugs capable of improving drug efficacy while minimizing toxicity.

Accordingly, development of targeted anticancer drugs capable of minimizing damage to normal cells will lead to a remarkable improvement in the therapeutic effect of the conventional chemotherapy or radiotherapy.

SUMMARY OF THE INVENTION

The present inventors intended to develop an anticancer prodrug that exists as a non-toxic prodrug of an active ingredient when provided in vivo or in vitro, but effectively releases the active ingredient resulting from cleavage of the prodrug by caspase activated only in a target area when the target area in the body is exposed to radiation of radioactive ray or UV for therapeutic purpose.

Accordingly, an object of the present invention is to provide an anticancer prodrug consisting of peptide of acetyl-SEQ ID NO: 1-linker-anticancer drug, which exists as a non-toxic prodrug but effectively releases the anticancer drug as an active ingredient resulting from cleavage of the prodrug under the presence of caspase activated in vivo by of radioactive ray or UV.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 1 is a diagram showing the anticancer prodrug according to one embodiment of the present invention;

FIG. 2 shows caspase-3 expression level depending on radiation dose and time;

FIGS. 10a to 10b are the results of MTT assay of the conventional AcDEVD-DOX that is disclosed in US Patent Publication No. 2007-0104719;

FIG. 12 is an image showing cellular uptake of the anticancer prodrug according to the present invention;

FIG. 14 is an image showing cellular uptake of the anticancer prodrug according to the present invention after radiation;

FIG. 15 is an image showing cellular uptake of the anticancer prodrug according to the present invention after UV treatment;

DETAILED DESCRIPTION OF THE PREFERRED EMBODIMENTS

Figure 3A:
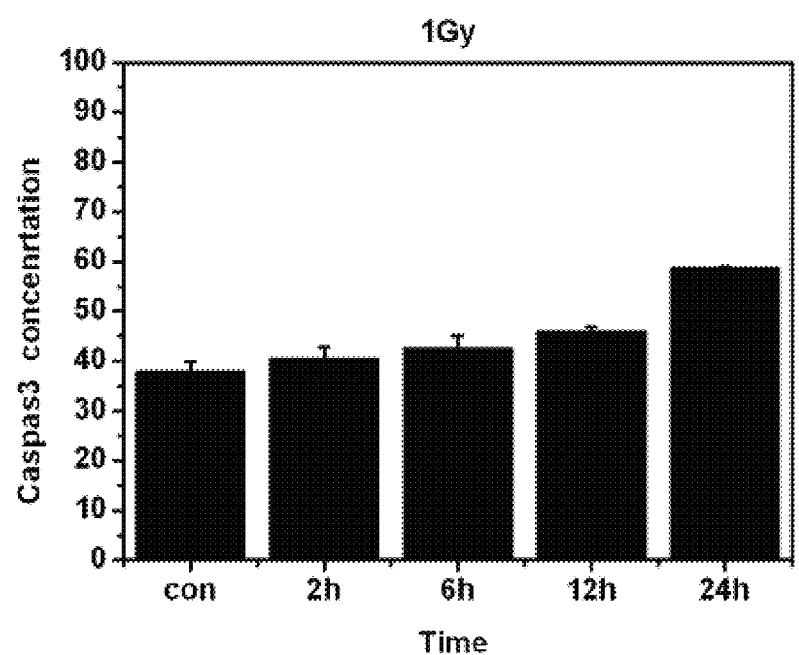
FIGS. 3a to 3c show caspase-3 activity depending on radiation dose and time.

In order to achieve the above object, an object of the present invention is to provide an anticancer prodrug that is prepared by linking an anticancer drug to a peptide inducing apoptosis, in which the peptide contains a caspase cleavage site and thus is cleaved thereby to topically release the anticancer drug as an active ingredient and consequently to exhibit anticancer efficacy.

Specifically, the present invention provides a prodrug composition including a peptide having acetyl-SEQ ID NO: 1, a linker, and an anticancer drug that are sequentially linked to each other, in which the peptide having acetyl-SEQ ID NO: 1 is cleaved by active caspase.

Further, the present invention provides a method for preparing the prodrug including the peptide having acetyl-SEQ ID NO: 1, the linker, and the anticancer drug that are sequentially linked to each other, including the steps of:

preparing a modified peptide, in which hydrogen of the carboxylic group of the side chain of aspartic acid (Asp) or glutamic acid is substituted with an allyl group and hydrogen of the amino group of the side chain of lysine (Lys) is substituted with an allyloxycarbony group in the peptide having acetyl-SEQ ID NO: 1;

linking a linker to the C-terminus of the modified peptide;
chemically combining the anticancer drug with the linker;
deprotecting the allyl group and the allyloxycarbony group of the modified peptide.

Further, the present invention provides an anticancer therapeutic kit, including the prodrug composition including the peptide having acetyl-SEQ ID NO: 1, the linker, and the anticancer drug that are sequentially linked to each other, in which the peptide having acetyl-SEQ ID NO: 1 is cleaved by caspase; and an apparatus for radiation of radioactive ray or UV to a subject in need who is administered with the prodrug so as to induce caspase activation in tumor cells.

Further, the present invention provides a site-specific anticancer therapy, including the steps of:

administering to a subject in need of anticancer therapy the prodrug composition including the peptide having acetyl-SEQ ID NO: 1, the linker, and the anticancer drug that are sequentially linked to each other, in which the peptide having acetyl-SEQ ID NO: 1 is cleaved by active caspase; and performing radiation of radioactive ray or UV to a subject who is administered with the prodrug using an apparatus for radiation of radioactive ray or UV so as to induce caspase activation in tumor cells.

Hereinafter, the present invention will be described in more detail.

The present invention provides an anticancer prodrug consisting of the peptide of acetyl-SEQ ID NO: 1 (KGDEVD)-linker-anticancer drug.

The anticancer prodrug according to the present invention is provided such that the DEVD amino acid sequence in the peptide sequence of SEQ ID NO. 1 (KGDEVD) is recognized by caspase, in particular, caspase-3, and cleaved thereby, and thus the anticancer drug as an active ingredient is released from the target area.

The linker used in the present invention may be any one selected from the group consisting of para-aminobenzyloxycarbonyl, aminoethyl-N-methylcarbonyl, aminobiphenylmethyloxycarbonyl, a dendritic linker and a cephalosporin-based linker, and preferably para-aminobenzyloxycarbonyl.

The anticancer drug used in the present invention may be any one selected from the group consisting of doxorubicin, paclitaxel, adriamycin, cisplatin, 5-fluorouracil, mitomycin, chlomomycin, bleomycin, peplomycin, daunorubicin, aclarubicin, neocarzinostatin, epirubicin, idarubicin and pirarubicin, and preferably doxorubicin.

More preferably, the anticancer prodrug according to the present invention consists of peptide of acetyl-SEQ ID NO: 1-para aminobenzyloxycarbonyl-doxorubicin.

Another specific embodiment of the present invention relates to a method for preparing the prodrug including the peptide having acetyl-SEQ ID NO: 1, the linker, and the anticancer drug that are sequentially linked to each other, including the steps of:

preparing a modified peptide, in which hydrogen of the carboxylic group of the side chain of aspartic acid (Asp) or glutamic acid is substituted with an allyl group and hydrogen of the amino group of the side chain of lysine (Lys) is substituted with an allyloxycarbony group in the peptide having acetyl-SEQ ID NO: 1;

linking a linker to the C-terminus of the modified peptide;
chemically combining the anticancer drug with the linker;
deprotecting the allyl group and the allyloxycarbony group of the modified peptide.

At first, the present inventors tried to perform hydrogenation of an anticancer drug, which is unstable in acid or base such as doxorubicin, without deprotecting a protecting group with an acidic and basic substance. However, as shown in the following Reaction Scheme 1, when Compound 6 was prepared, doxorubicin was reduced by hydrogenation. The following Reaction Scheme 1 represents a preparation process of the anticancer prodrug by other method than the method of the present invention.

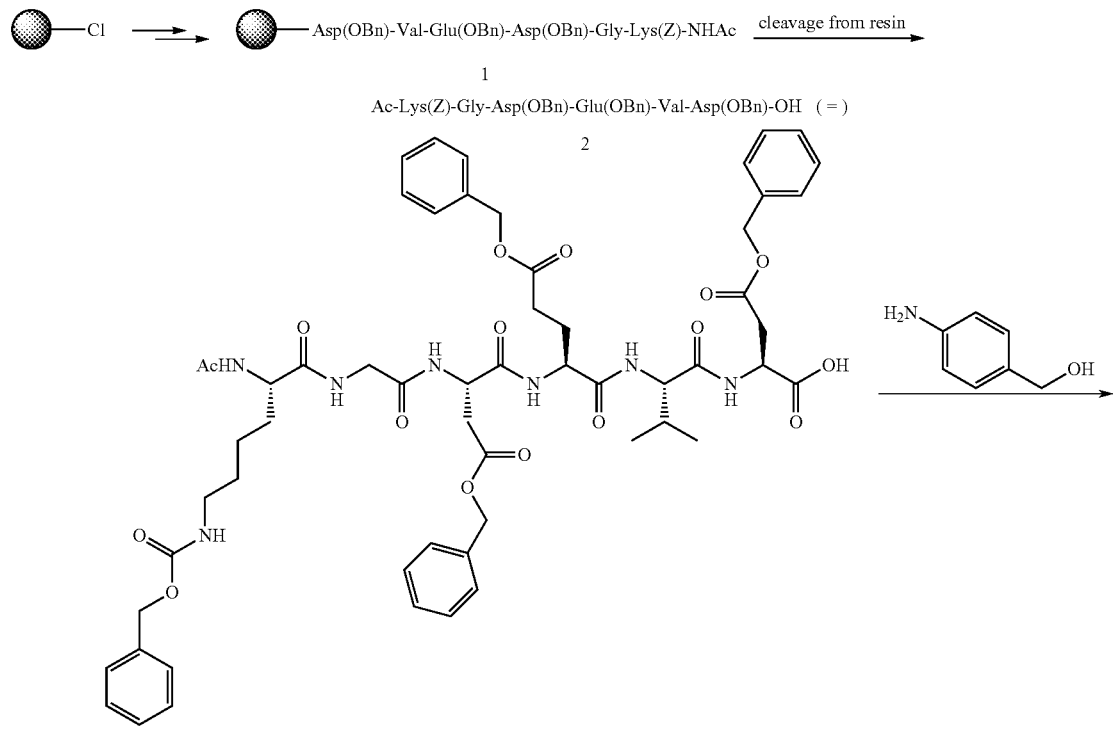

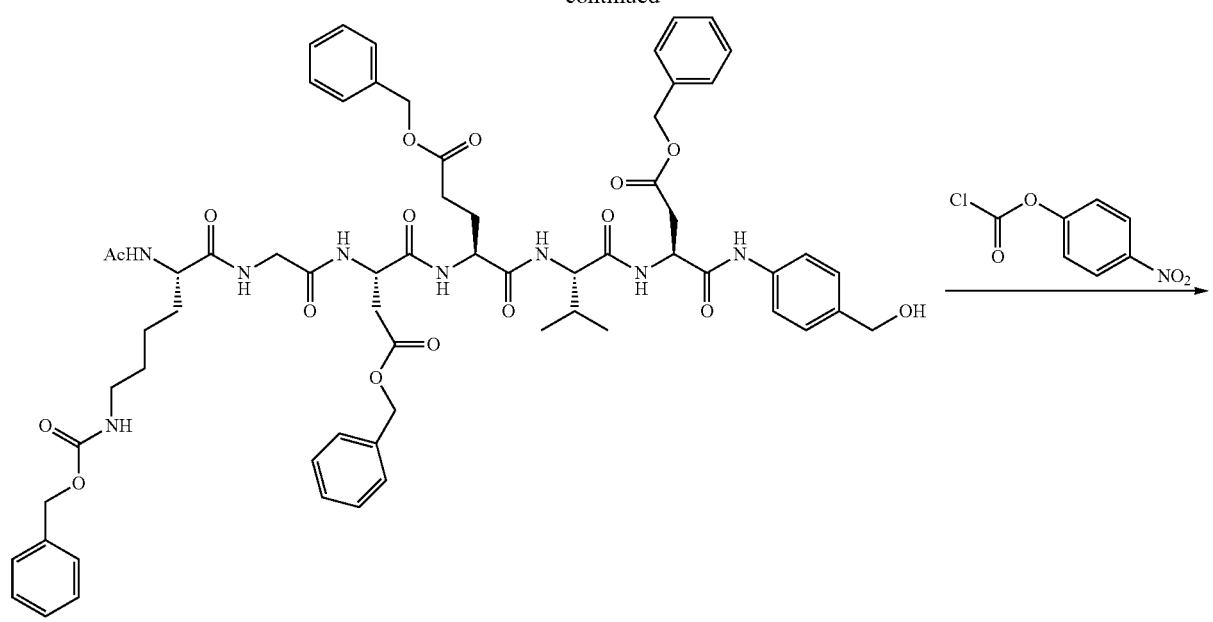
4
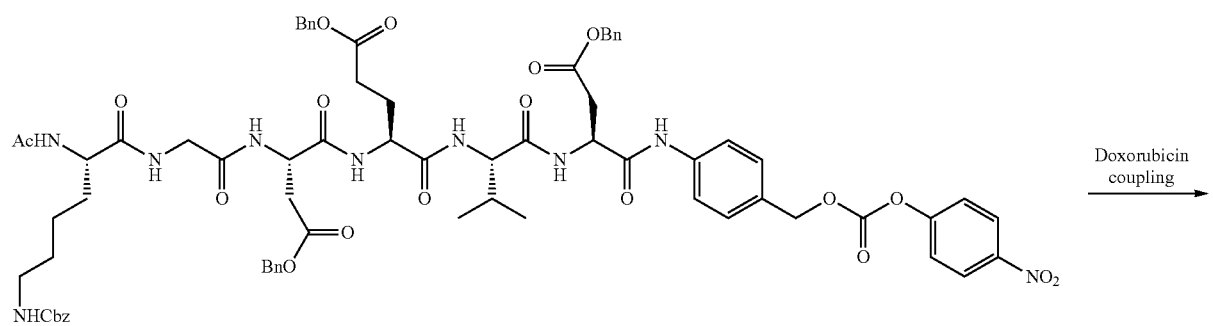
5
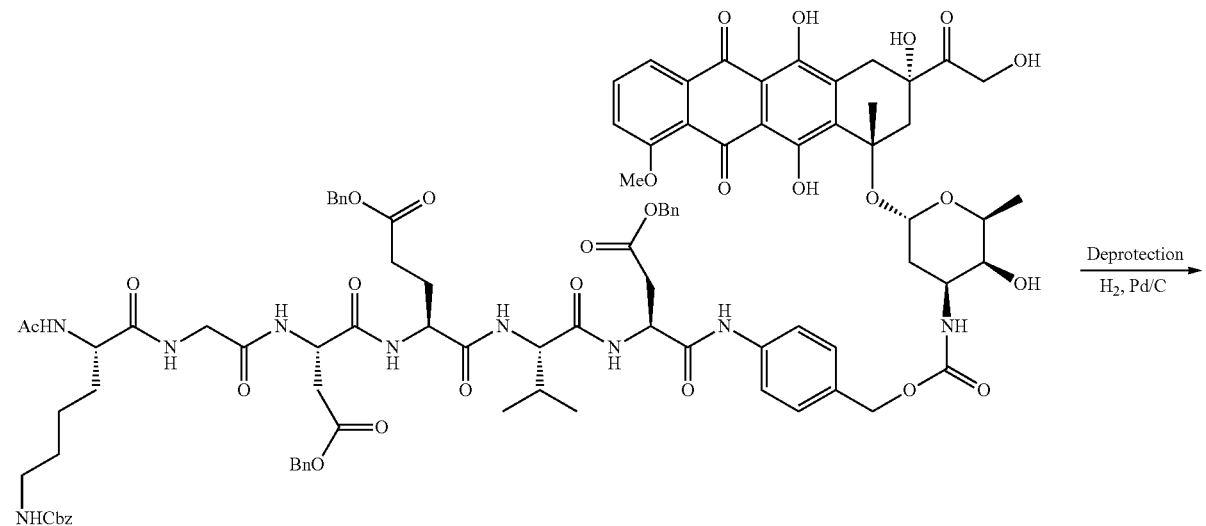
6

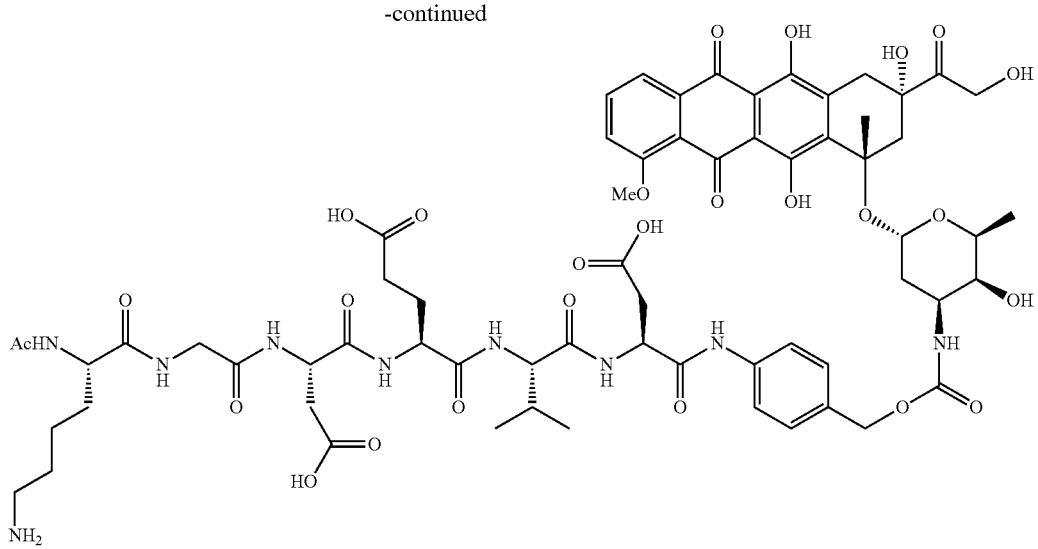

7
decomposed

As in Reaction Scheme 2, it was also tried that a carbonate group was prepared and reacted with doxorubicin in advance, and then the peptide was coupled thereto for the entire deprotection. However, doxorubicin was decomposed during the deprotection process of a carboxybenzyloxy (Cbz) group for the preparation of Compound 13.

The following Reaction Scheme represents a preparation process of the anticancer prodrug by other method than the method of the present invention.

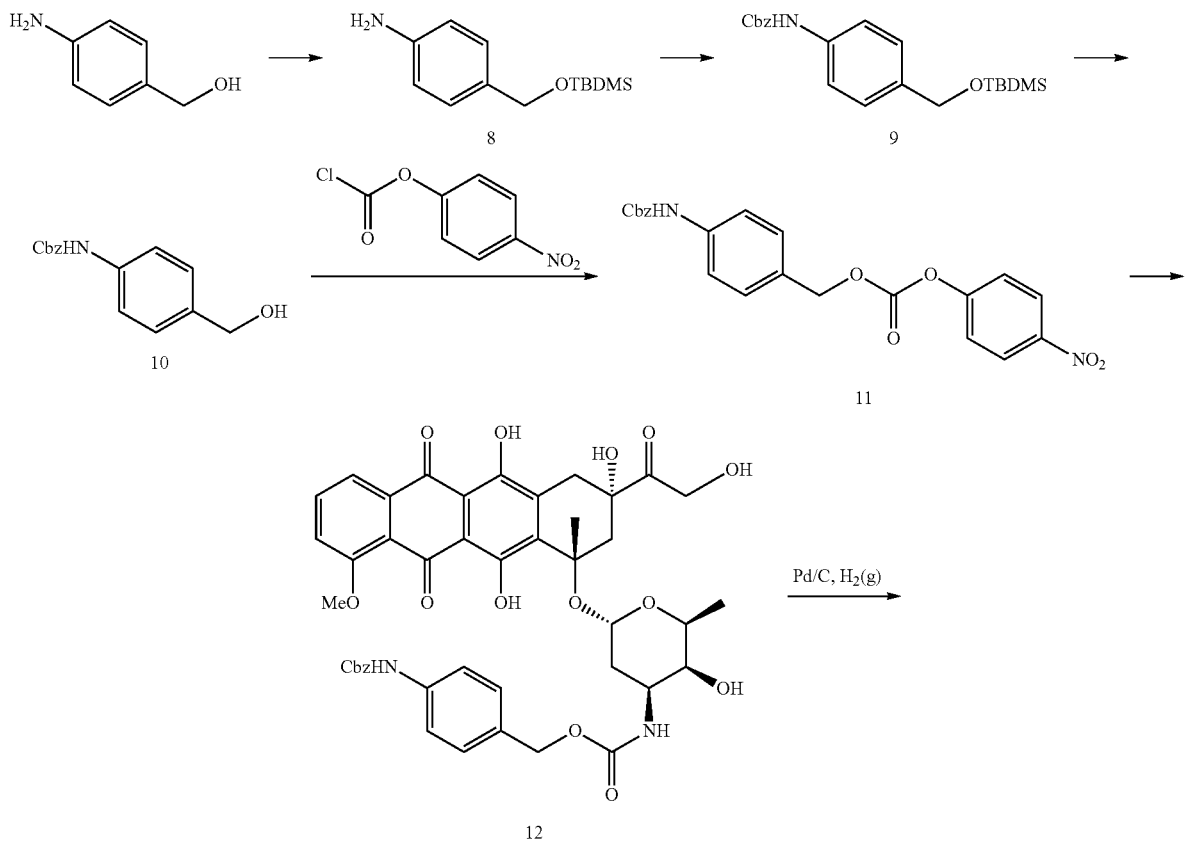

-continued
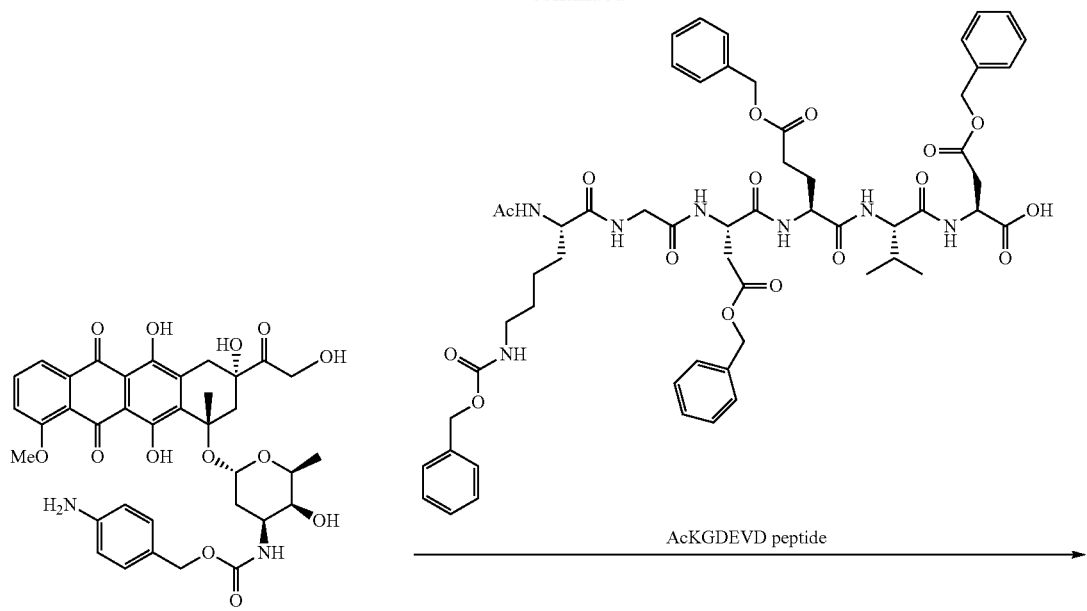
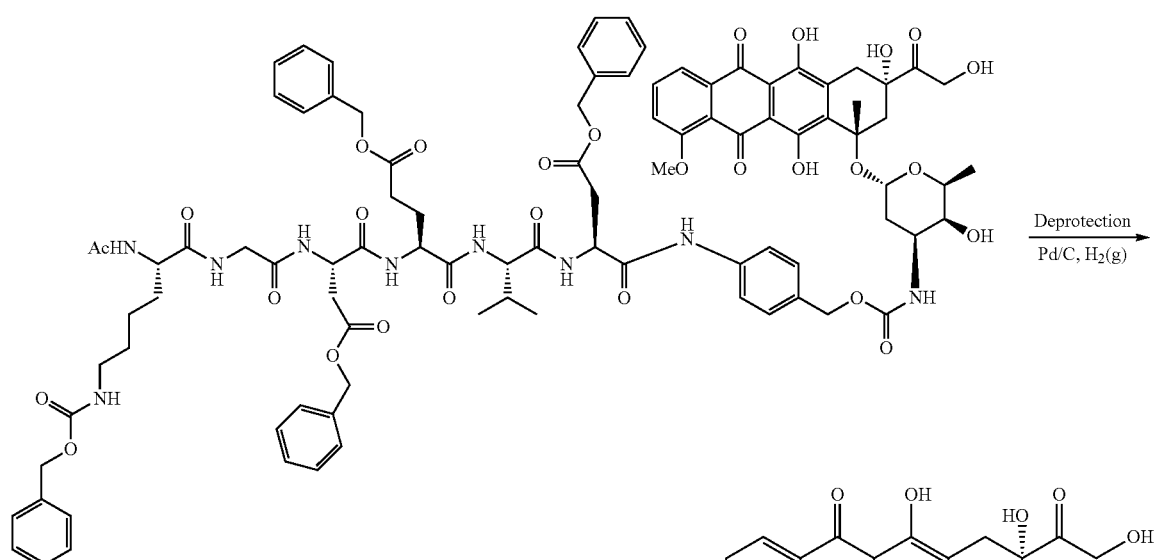
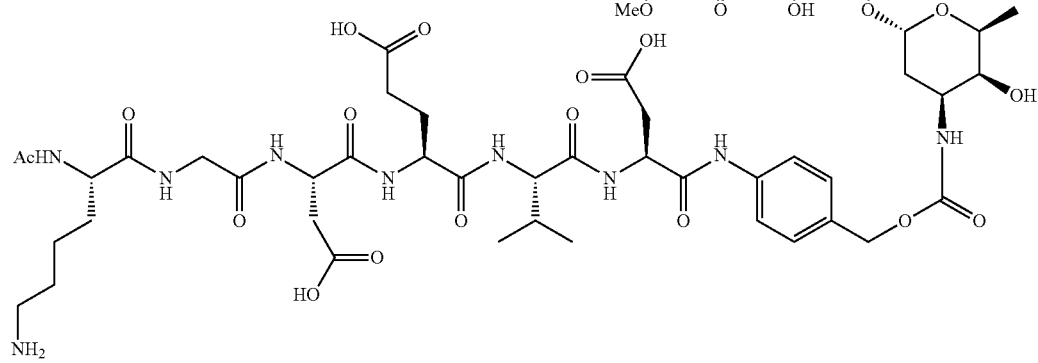

Use of $Et_3SiH$ and $PdCl_2$ was also tried as another method of removing the cbz group without hydrogenation. However, a desired compound was not obtained, even though the reaction was performed at room temperature because the compound was not stable under reflux conditions as in the literature. The reaction was also tried at room temperature using $t\text{-}BuMe_2SiH$ and $Pd(OAc)_2$, but the reaction did not proceed.

Meanwhile, the present inventors considered a method of modifying the protecting group of the peptide, and finally developed the allyl group and the allyloxycarbonyl (alloc) group that are deprotectable under relatively stable conditions without affecting other functional groups, thereby completing the present invention.

The specific preparation process of the anticancer prodrug of the present invention is illustrated in the following Reaction Scheme 3, and a detailed description thereof will be given. The following Reaction Scheme 3 represents the preparation process of the anticancer prodrug according to one embodiment of the present invention.

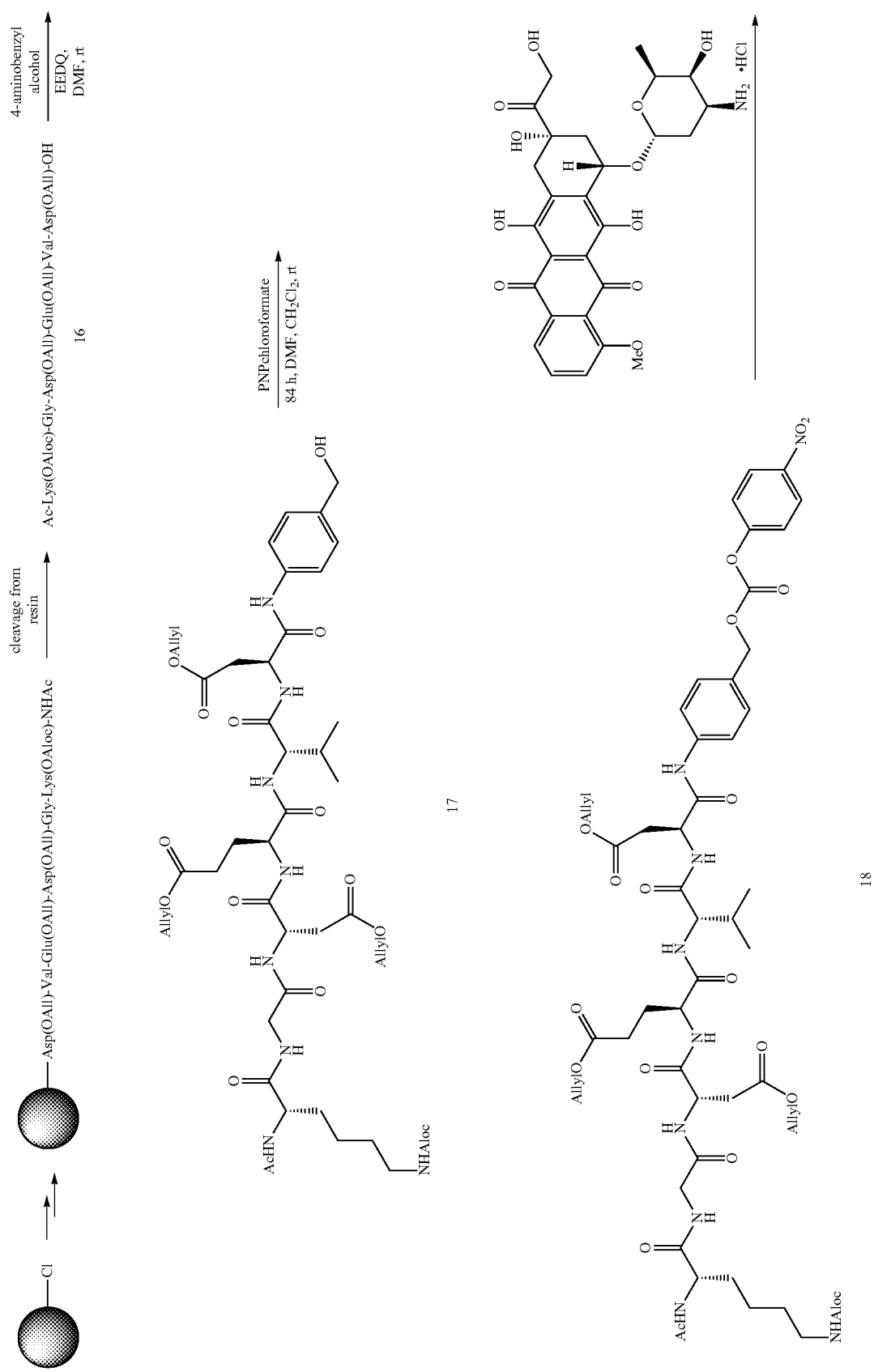

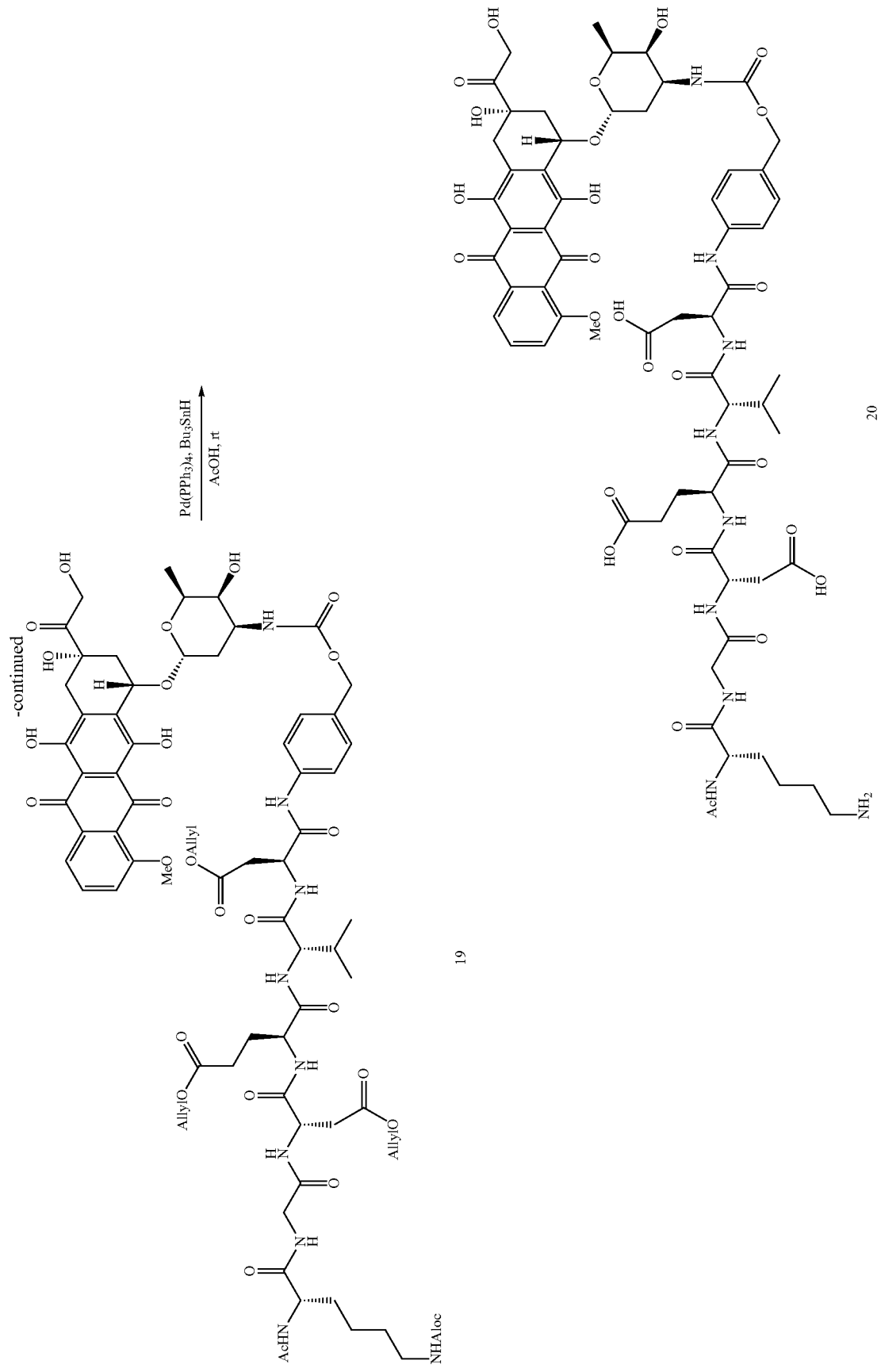

For preparation of the anticancer prodrug according to the present invention, Ac-Lys(OAloc)-Gly-Asp(OAll)-Glu(OAll)-Val-Asp(OAll)-OH (16) was first prepared as in Reaction Scheme 3. That is, Compound 16 was prepared through the steps of coupling amino acids to a resin, synthesizing peptides, performing acetylation of amine groups, and releasing the peptides from the resin. Compound 16 was treated with 4-aminobenzyl alcohol and EEDQ (2-Ethoxy-1-ethoxycarbonyl-1,2-dihydroquinoline) in the presence of DMF (Dimethyl Fumarate) at room temperature to prepare Ac-Lys(OAloc)-Gly-Asp(OAll)-Glu(OAll)-Val-Asp(OAll)-PABOH (17). Compound 17 was treated with 4-nitrophenyl chloroformate and lutidine in the presence of anhydrous ethylene chloride to prepare Ac-Lys(OAloc)-Gly-Asp(OAll)-Glu(OAll)-Val-Asp(OAll)-PABC (18).

Compound 18 was treated with doxorubicin at room temperature in the dark to prepare Ac-Lys(OAloc)-Gly-Asp(OAll)-Glu(OAll)-Val-Asp(OAll)-PABC-DOX (19). Compound 19 was treated with Pd(PPh$_3$)$_4$, Bu$_3$SnH and acetic acid to prepare Ac-Lys-Gly-Asp-Glu-Val-Asp-PABC-DOX (20, AcKGDEVD-PABC-DOX) according to the present invention.

Progress of the entire reaction was monitored by C-18 reverse-phase HPLC, and preparative HPLC column was used for separation of the compounds. Acetonitrile and 0.1% TFA (trifluoroacetic acid) in water were used as a solvent.

When the anticancer prodrug according to the present invention is prepared as a pharmaceutical composition, a proper carrier, excipient, or diluent typically used in the pharmaceutical composition may be further included.

Examples of the carrier, excipient, or diluent usable in the present invention may include lactose, dextrose, sucrose, sorbitol, mannitol, xylitol, erythritol, maltitol, starch, acacia rubber, alginate, gelatin, calcium phosphate, calcium silicate, cellulose, methyl cellulose, microcrystalline cellulose, polyvinyl pyrrolidone, water, methylhydroxybenzoate, propylhydroxybenzoate, talc, magnesium stearate, minerals or the like.

The pharmaceutical composition may be formed in an oral formation such as a powder, a granule, a tablet, a capsule, a suspension, an emulsion, a syrup, or an aerosol, an external-use formulation, a suppository formulation, or a sterilized injection solution formulation according to the respective conventional methods.

These formulations may be prepared by using a conventionally available diluent or excipient, such as a filler, an extender, a binder, a wetting agent, a disintegrant, a surfactant or the like. Examples of a solid formulation for oral administration include a tablet, a pill, a powder, a granule, a capsule or the like. These solid formulations are manufactured by mixing the compound with at least one excipient, for example, starch, calcium carbonate, sucrose, lactose, gelatin or the like.

In addition to the simple excipient, a lubricant such as magnesium stearate or talc may also be used. A liquid formulation for oral administration includes a suspension, a liquid for internal use, an emulsion and a syrup. The liquid formulation may include various excipients, for example, a wetting agent, a sweetener, an aromatic, a preservative or the like, in addition to water that is a commonly available simple diluent, and liquid paraffin.

A formulation for parenteral administration includes a sterilized aqueous solution, a water-insoluble solution, a suspension, an emulsion, a lyophilized formulation and a suppository. The non-aqueous solution formulation and the suspension formulation may be propylene glycol, polyethylene glycol, a plant oil such as olive oil, or injectable ester such as ethyloleate. A base for the suppository formulation may be witepsol, macrogol, tween 61, cacao butter, laurin butter, glycerogelatin or the like.

When the anticancer prodrug according to the present invention is prepared as a pharmaceutical composition, the amount of the anticancer prodrug included in the pharmaceutical composition may vary depending on the age, gender, and weight of a patient, and the pharmaceutical composition may be administered once or several times for a day. The administration dose thereof may vary depending on administration route, severity of disease, gender, weight, age or the like. Accordingly, the scope of the present invention is not limited to the administration dose in any respect.

The pharmaceutical composition may be administered to mammals, such as rats, mice, livestock, or humans, via various routes. All modes of administration are contemplated, for example, administration can be made orally, rectally or by intravenous, intramuscular, subcutaneous, epidural or intracerebroventricular injection.

Further, the pharmaceutical composition of the present invention relates to a novel formulation for improving bioavailability of the conventional anticancer drug that has secured safety, and thus can be used safely.

Still another specific embodiment of the present invention provides an anticancer therapeutic kit, including the prodrug composition including the peptide having acetyl-SEQ ID NO: 1, the linker, and the anticancer drug that are sequentially linked to each other, in which the peptide having acetyl-SEQ ID NO: 1 is cleaved by active caspase; and an apparatus for radiation of radioactive ray or UV to a subject who is administered with the prodrug so as to induce caspase activation in tumor cells.

According to the present invention, when an inactive form of the anticancer prodrug is administered, the anticancer prodrug is accumulated at the target site and the peptide is decomposed by radiation, thereby releasing an active form of the anticancer drug at the target site. Accordingly, the anticancer therapeutic effect can be maximized with a low dose of anticancer drug and radiation while minimizing damage to normal cells.

After administration of the anticancer prodrug according to the present invention, no side-effects are observed, but a weak apoptotic effect is induced in the cancer tissue because of the low therapeutic effect due to a low dose of anticancer drug and radiation.

The weak apoptotic effect induced under general conditions shows no significant anticancer therapeutic effect, but the apoptotic effect induced under accumulation of the anticancer prodrug of the present invention in the tumor tissue changes the anticancer drug from an inactive to active form. Therefore, the active anticancer drug selectively and gradually amplified in the tumor tissue shows high cytotoxicity, consequently resulting in highly efficient targeted therapy.

High anticancer therapeutic effect can be achieved with a much lower dose of anticancer drug and radiation while minimizing damage to normal cells, thereby remarkably reducing the side-effects caused by the conventional chemotherapy and radiotherapy. Further, the anticancer prodrug of the present invention is a new concept of anticancer drug, which targets cancer cells and is specifically activated during apoptosis to show additional cytotoxicity on cancer cells, thereby providing a new promising treatment option capable of dramatically increasing the therapeutic effects of the conventional chemotherapy and radiotherapy.

In the present invention, the apparatus for radiation of radioactive ray or UV may be any one typically used in the cancer treatment, as long as the apparatus for radiation of radioactive ray or UV is able to induce caspase activation due to apoptosis in a subject in need of treatment, but it is not particularly limited thereto. A proper radiation dose according to the present invention may be within the radiation dose range generally used in radiotherapy. For example, considering in vivo result that apoptosis was not induced at about 1 Gy when administered with no devd-dox, the radiation dose may be 1 Gy or higher. If the radiation dose is 5 Gy or higher, apoptosis is induced, but other tissues can be damaged. Thus, a higher dose is substantially meaningless. Preferably, the radiation dose may be 1 Gy to 5 Gy. A dose of UV treatment may be also within the range of general UV treatment, for example, 1 J/m$^2$ to 50 J/m$^2$.

Hereinafter, the preset invention will be described in more detail with reference to the following Examples. However, the present invention is not limited to these Examples.

EXAMPLE 1

Preparation of Anticancer Prodrug AcKGDEVD-PABC-DOX

1. Ac-Lys(OAloc)-Gly-Asp(OAll)-Glu(OAll)-Val-Asp(OAll)-OH (16)

1) Coupling of Amino Acids to Resin 2-chlorotritylchloride resin (TCP) was swollen in $CH_2Cl_2$ for 40 minutes, and then Fmoc-Asp(OAll)-OH (1.3 eq) and DIEA (Diisopropylethylamine, 3.3 eq) dissolved in $CH_2Cl_2$ were added thereto. After 5 minutes, DIEA was further added, and reacted for 1 hour. After 1 hour, methanol was added thereto, and further reacted for 20 minutes, and the resin was washed with $CH_2Cl_2$ and DMF for each 5 minutes three times and twice, respectively. Fmoc-functional groups were removed with shaking using a 20% piperidine (20 ml) solution for 5 minutes. After the reactant was removed, the resin was washed with DMF and $CH_2Cl_2$ for each 5 minutes three times, respectively.

2) Synthesis of Peptide

To synthesize peptides, Fmoc-Val-OH (3 eq) and TBTU (3 eq), and HOBT (3 eq) in DMF and $CH_2Cl_2$ were first added to the aspartic acid-coupled resin, and DIEA (8 eq) was added thereto, followed by shaking for 1 hour. The completion of the reaction was monitored by Kaiser test, and then Fmoc-functional groups were removed with shaking using the 20% piperidine solution for 5 minutes, as described above. In the same manner, the remaining amino acids, Fmoc-Glu(OAll)-OH, Fmoc-Asp(OAll)-OH, Fmoc-Gly-OH, and Fmoc-Lys(OAloc)-OH were reacted, and Fmoc-functional groups were removed.

3) Acetylation of Amine Group

For protection of free amine groups with acetyl groups, each 3 eq of DMAP and $Ac_2O$ was used and dissolved in 20 mL of DMF, and then stirred for 1 hour. The completion of the reaction was monitored by Kaiser test, and the resin was washed with DMF and $CH_2Cl_2$ for each 5 minutes three times, respectively.

4) Release of Peptide from Resin

For removal, the resin was dissolved in a solvent mixture of $CH_2Cl_2$:AcOH:TFE=6:3:1, and stirred at room temperature for 2 hours. Then, the solvent was removed, followed by crystallization with ether and filtration under reduced pressure. Finally, resin-removed peptides were obtained.

ESI-MS: [M−H$^+$]=906.2

2. Ac-Lys(OAloc)-Gly-Asp(OAll)-Glu(OAll)-Val-Asp(OAll)-PABOH (17)

Ac-Lys(OAloc)-Gly-Asp(OAll)-Glu(OAll)-Val-Asp(OAll)-OH (344 mg, 0.38 mmol), 4-aminobenzyl alcohol (2 eq), and EEDQ (2 eq) were dissolved in anhydrous DMF (11 mL), and then stirred at room temperature for 24 hours. After the solvent was completely removed, the peptides (322 mg, 84%) were crystallized with ether to give Compound 17.

ESI-MS: [M+Na$^+$]=1035.7

3. Ac-Lys(OAloc)-Gly-Asp(OAll)-Glu(OAll)-Val-Asp(OAll)-PABC (18)

Ac-Lys(OAloc)-Gly-Asp(OAll)-Glu(OAll)-Val-Asp(OAll)-PABOH (322 mg, 0.318 mmol) and 4-nitrophenyl chloroformate (1.2 eq) were dissolved in anhydrous $CH_2Cl_2$ (10 mL), and then 2,6-lutidine (3 eq) was added thereto, followed by stirring at room temperature. After 2 hours, anhydrous DMF (2 mL) was added to the reactant and 2,6-lutidine (2 eq) was also added. After 24 hours and 27 hours, and after 46 hours, 2,6-lutidine (4.75 eq) and 4-nitrophenyl chloroformate (1 eq) were added, respectively, followed by stirring at room temperature. After 84 hours, a sodium bicarbonate aqueous solution was added to complete the reaction.

The reactants were extracted with ethyl acetate three times, and the organic layer was washed with a 0.5 M citric acid aqueous solution and a sodium bicarbonate aqueous solution, and brine. The organic layer thus obtained was allowed to pass through an anhydrous sodium sulfate layer to remove residual moisture. The solvent was removed under reduced pressure, followed by crystallization with ether. Finally, Compound 18 was obtained. prep. HPLC was performed for separation (77 mg, 20.5%).

[HPLC separation conditions: C-18 reverse-phase 22 mm i.d.×250 mm column; flow-rate 10 mL/min; 20~53% (acetonitrile) in (water+0.1% TFA) linear gradient elution over 30 min.; retention time 27 min], ESI-MS: [M+Na$^+$]=1200.54

4. Ac-Lys(OAloc)-Gly-Asp(OAll)-Glu(OAll)-Val-Asp(OAll)-PABC-DOX (19)

Ac-Lys(OAloc)-Gly-Asp(OAll)-Glu(OAll)-Val-Asp(OAll)-PABC (77 mg, 0.065 mmol) and doxorubicin hydrochloride (1.2 eq) were dissolved in anhydrous DMF (8 mL), and then DIEA (5.4 eq) was added, and the flask was wrapped with foil to block light, followed by stirring at room temperature for 16 hours. The solvent was removed under reduced pressure, and then prep. HPLC was performed to separate Ac-Lys(OAloc)-Gly-Asp(OAll)-Glu(OAll)-Val-Asp(OAll)-PABC-DOX (non-crystalline orange-red solid, 76 mg, 74%) as Compound 19.

[HPLC separation conditions: C-18 reverse-phase 22 mm i.d.×250 mm column; flow-rate 10 mL/min; 20~100% (acetonitrile) in (water+0.1% TFA) linear gradient elution over 50 min.; retention time 34 min], ESI-MS: [M+Na$^+$]=1605.06

5. Ac-Lys-Gly-Asp-Glu-Val-Asp-PABC-DOX (20, AcKGDEVD-PABC-DOX)

Ac-Lys(OAloc)-Gly-Asp(OAll)-Glu(OAll)-Val-Asp(OAll)-PABC-DOX (76 mg, 0.048 mmol) and Pd(PPh$_3$)$_4$ (0.2 eq) were dissolved in anhydrous DMF (7.6 mL), and then acetic acid (15 eq) and tributyltin hydride (13 eq) were added to the reactants. The mixture was stirred at room temperature for 1 hour, and then the solvent was removed under reduced pressure. Prep. HPLC was performed to separate and obtain deprotected Ac-Lys-Gly-Asp-Glu-Val-Asp-PABC-DOX (non-crystalline deep orange-red solid, 35 mg, 53%). The diagram for apoptosis-sensitive anticancer prodrug according to the present Example is as shown in FIG. 1.

[HPLC separation conditions: C-18 reverse-phase 22 mm i.d.×250 mm column; flow-rate 10 mL/min; 20~100% (acetonitrile) in (water+0.1% TFA) linear gradient elution over 60 min.; retention time 21 min], ESI-MS: [M+H⁺]=1378.4

EXAMPLE 2

Radiation Dose and Time of Radioactive Ray

Figure 5:
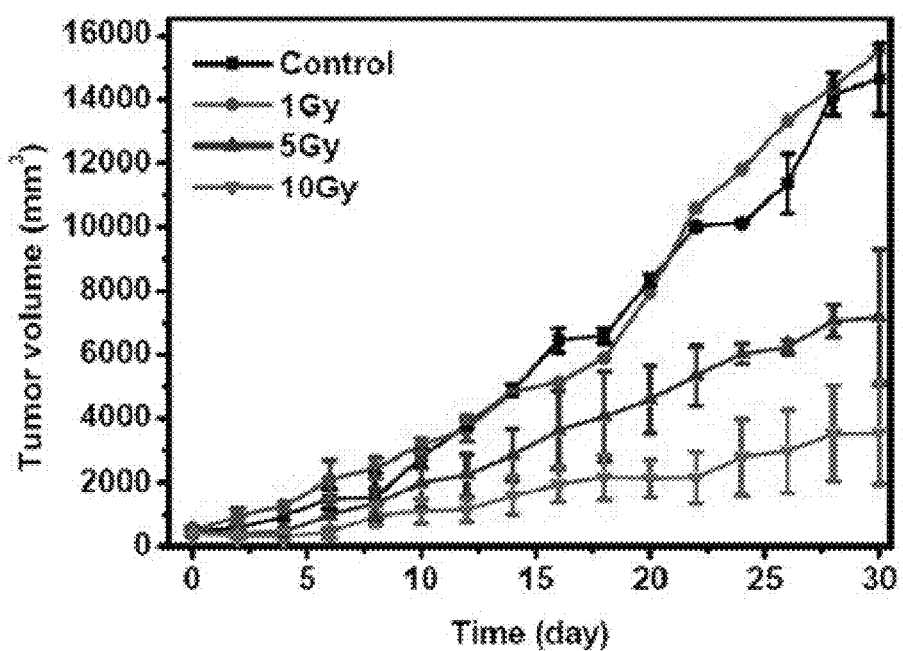
FIG. 5 shows tumor therapeutic effect depending on radiation dose.
Figure 6:
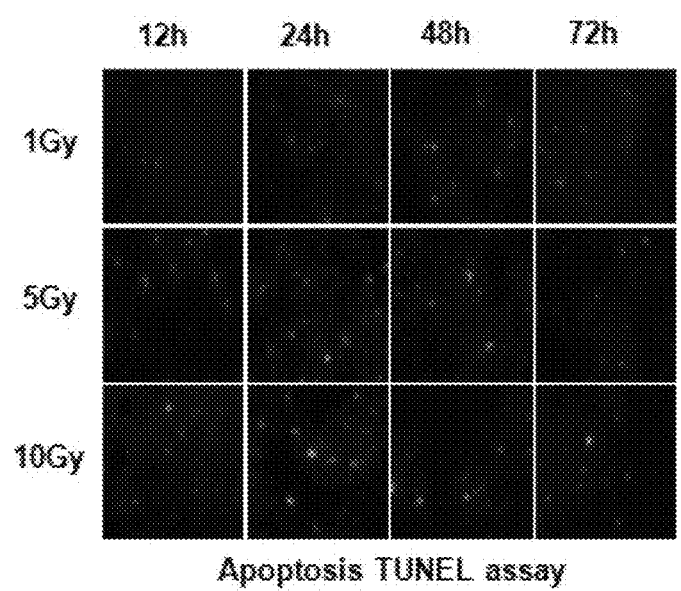
FIG. 6 shows apoptosis in tissues depending on radiation dose and time.
Figure 7:
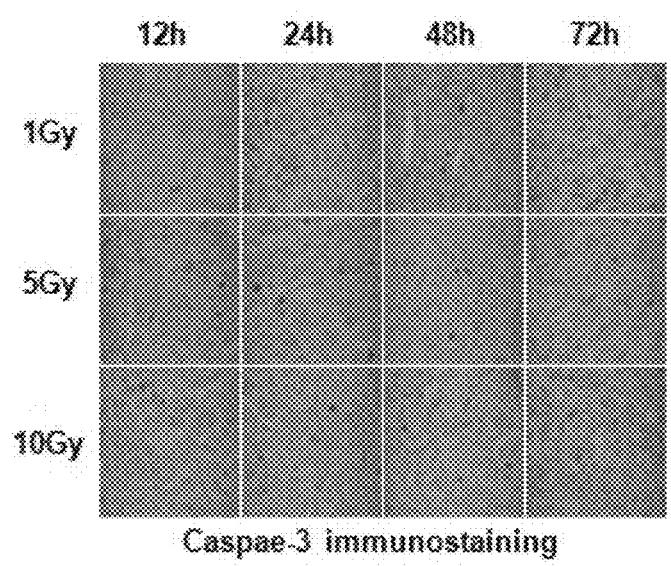
FIG. 7 is the result of IHC showing caspase-3 expression levels in tissues after radiation.

After radiating radioactive ray to cancer cells, time-dependent expression level and activity of caspase-3 in apoptosis-induced cells were quantified, and the results are shown in FIG. 2 and FIGS. 3a to 3c. After radiation, the degree of apoptosis induced in cancer cells was examined, and shown in FIG. 4a. Tumor growth and body weight were measured in the cancer-transplanted animal models after radiation, and the tumor-inhibitory effect was shown in FIG. 5. After radiation, tumor tissues were removed at predetermined time intervals, and apoptosis in the tissues were analyzed by TUNEL, and the results are shown in FIG. 6. The caspase-3 expression levels in the tissues were examined by IHC, and the results are shown in FIG. 7.

2.1. Quantification of Expression Level and Activity of Caspase-3 in Radiated Cancer Cells Western blot analysis of caspase-3 activated in cancer cells through the apoptotic signaling pathway after radiation was performed to examine its expression.

That is, 3×10⁵ of SCC (Squamous cell carcinoma) 7 cells were prepared, and apoptosis was induced by radiation at a dose of 1 Gy, 5 Gy, or 10 Gy. Protein sampling was performed at each time point (2 h, 6 h, 12 h, 24 h, 48 h), and proteins were separated using a 12% SDS-polyacrylamide gel, and transferred. Then, the membrane was washed with PBS twice, and blocked with 10% skim milk for 40 minutes. The membrane was treated with primary antibodies (caspase-3 1:400, β-actin 1:10000) at 4° C. overnight, and then treated with secondary antibodies (anti-rabbit or anti-mouse IgG HRP conjugate 1:2000) at room temperature for 1 hour. Expression of caspase-3 was examined using an ECL kit and an X-ray film. As a result, apoptosis-induced cancer cells by radiation increased caspase-3 expression in a time- and radiation dose-dependent manner, as shown in FIG. 2.

The activity of caspase-3 that was activated in cancer cells through the apoptotic signaling pathway after radiation was examined. That is, 3×10⁵ of SCC 7 cells were prepared, and apoptosis was induced by radiation at a dose of 1 Gy, 5 Gy, 10 Gy, 15 Gy, or 20 Gy. Protein sampling was performed at each time point (2 h, 6 h, 12 h, 24 h), and proteins sampled in a 96-well plate were analyzed using a caspase-3 assay kit and an ELISA reader.

Figure 3B:
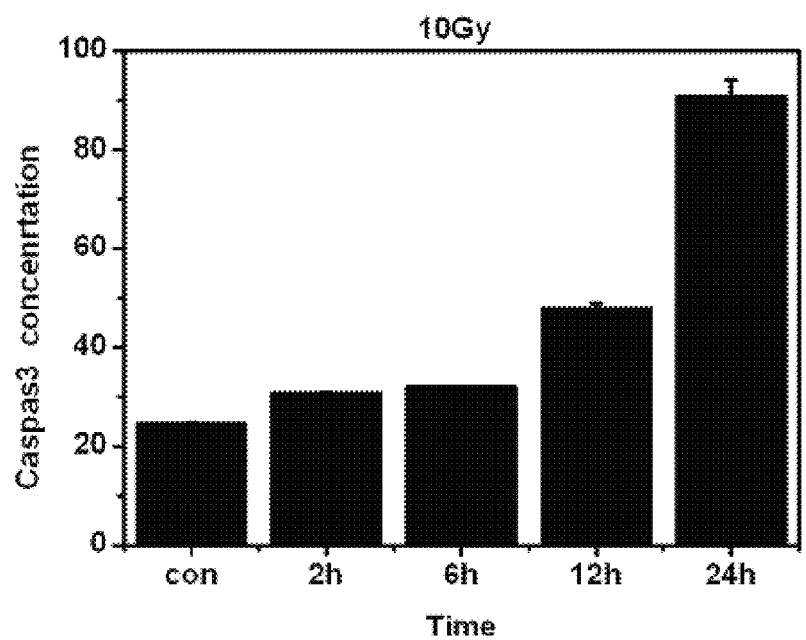
Figure 3C:
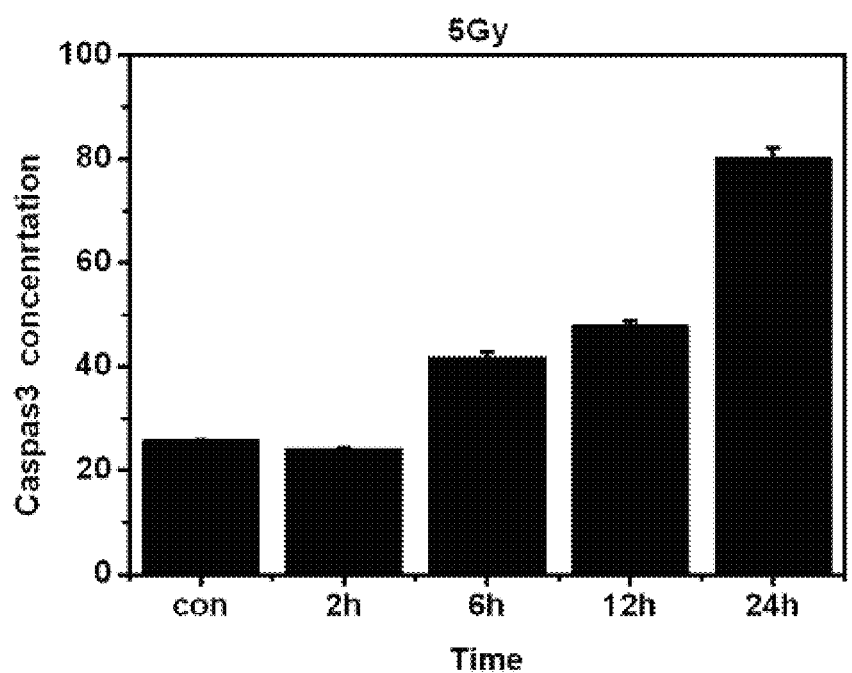

As shown in FIGS. 3a to 3c, apoptosis-induced cancer cells by radiation increased caspase-3 expression in a time- and radiation dose-dependent manner.

2.2 Apoptosis of Cancer Cells Radiated by Radioactive Ray

Apoptosis induced in cancer cells by radiation was examined by Flow cytometery (FACScan).

Figure 4:
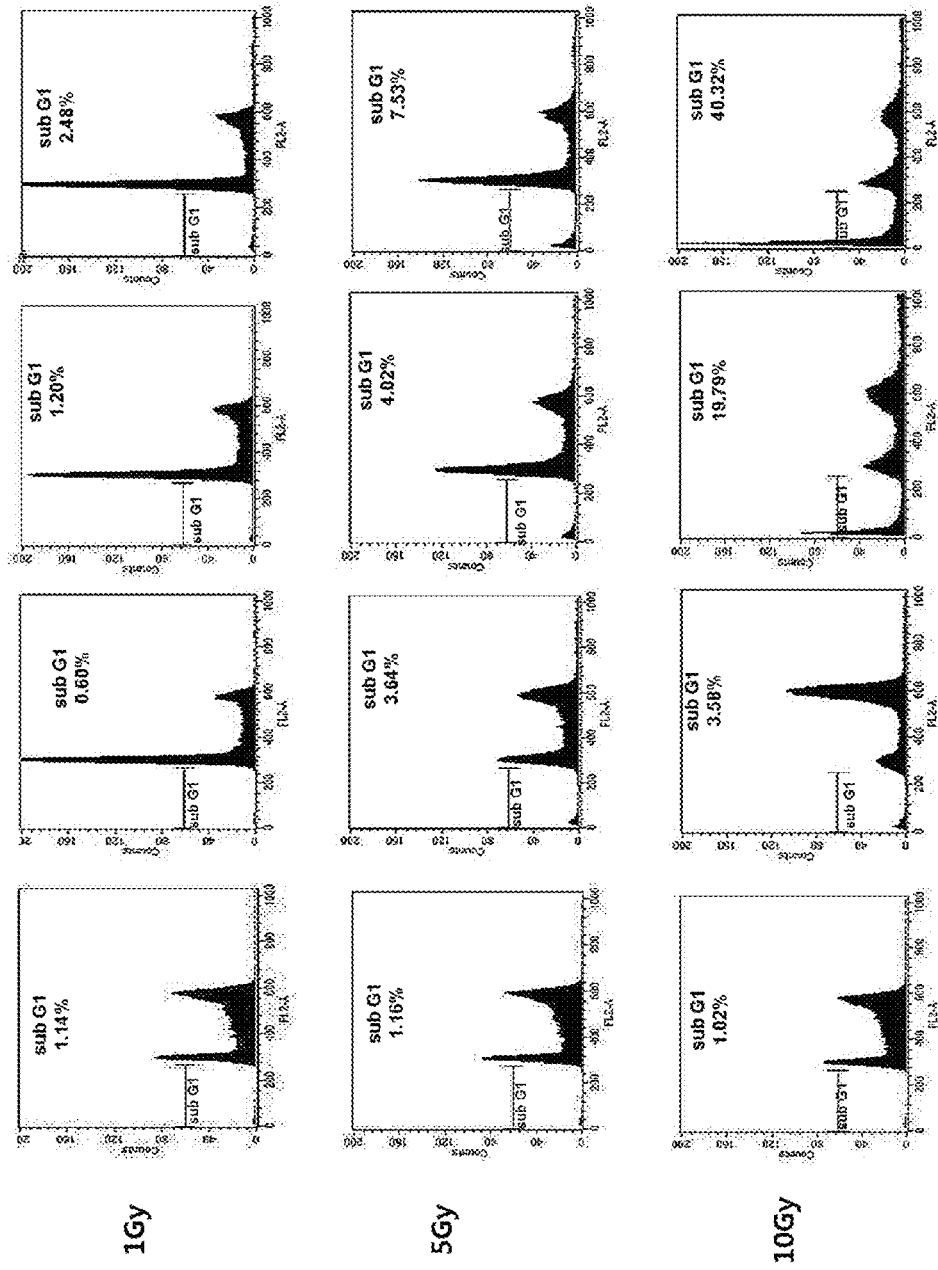
FIG. 4 shows apoptosis depending on radiation dose and time.

That is, 5×10⁴ of SCC 7 cells were prepared, and apoptosis was induced by radiation at a dose of 1 Gy, 5 Gy, 10 Gy, 15 Gy, or 20 Gy. Cells were sampled at each time point (12 h, 24 h, 48 h, 72 h). The cells were washed with PBS, and fixed in 70% ethanol. Then, the cells were treated with PBS-containing propidium iodide (50 μg μg/ml) and RNaseA (100 μg/ml) at room temperature for 30 minutes, and apoptosis was measured using a flow cytometery. The results are shown in FIG. 4.

2.3. Anti-Tumor Therapeutic Effect and Apoptosis in Tumor Animal Model

Anti-tumor therapeutic and apoptotic effects were examined in cancer cell-transplanted animal models, after radiation.

That is, tumor mouse models transplanted with SCC 7 cell line were radiated using a gamma knife by varying the radiation dose (1 Gy, 5 Gy, 10 Gy, 15 Gy, 20 Gy, 25 Gy). After radiation, in order to examine inhibitory effect on tumor, tumor growth and body weight were measured and the results are shown in FIG. 5.

12 h, 24 h, 48 h, 72 h after radiation, tumor tissues were removed, and apoptosis in the tissues was analyzed by TUNEL, and the results are shown in FIG. 6. 12 h, 24 h, 48 h, 72 h after radiation, tumor tissues were removed, and caspase-3 expression levels in the tissues were examined by IHC (see FIG. 7).

EXAMPLE 3

Analysis of Anti-Tumor Therapeutic Effect of Anticancer Prodrug

The anticancer prodrug (KGDEVD-DOX) prepared in Example 1 was injected, and then cells were radiated at a dose of 5 Gy for 5 minutes to examine anti-tumor therapeutic effect of the drug.

In detail, tumor mouse models transplanted with SCC 7 cell line were radiated (5 Gy) using a gamma knife. 24 hr after radiation, 3 mg/kg of the anticancer prodrug of Example 1 was administered into the animals via intravenous injection. After 2 days, the same dose (3 mg/kg) of the anticancer prodrug was injected into the animals. Tumor growth and body weight were measured every day until the experiments were terminated after radiation.

Figure 8:
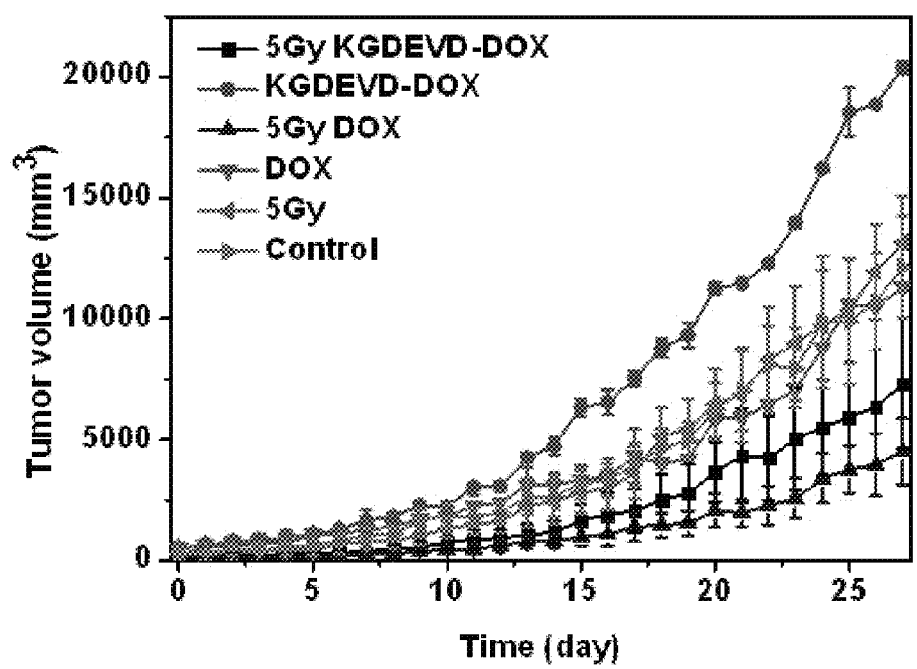
FIG. 8 shows therapeutic effect of the anticancer drug that is released by caspase-3 expressed after radiation.
Figure 9A:
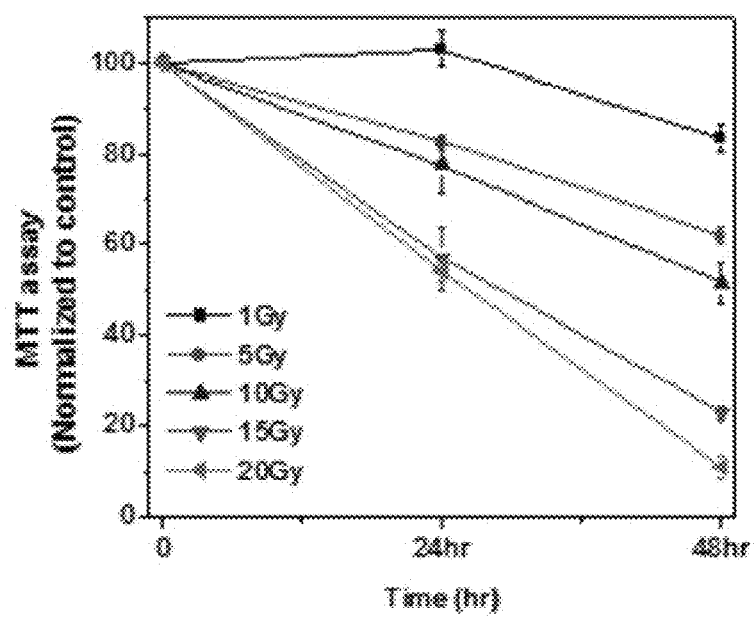
FIGS. 9a to 9f are the results of MTT assay of the anticancer prodrug according to the present invention.
Figure 9B:
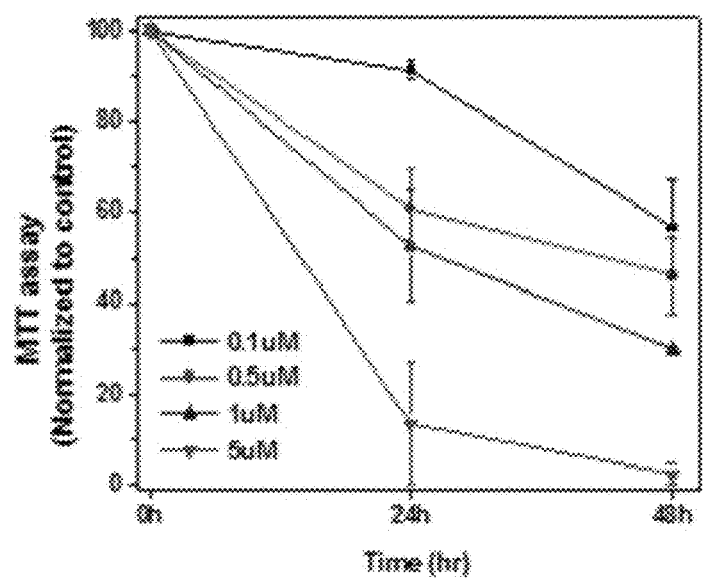
Figure 9C:
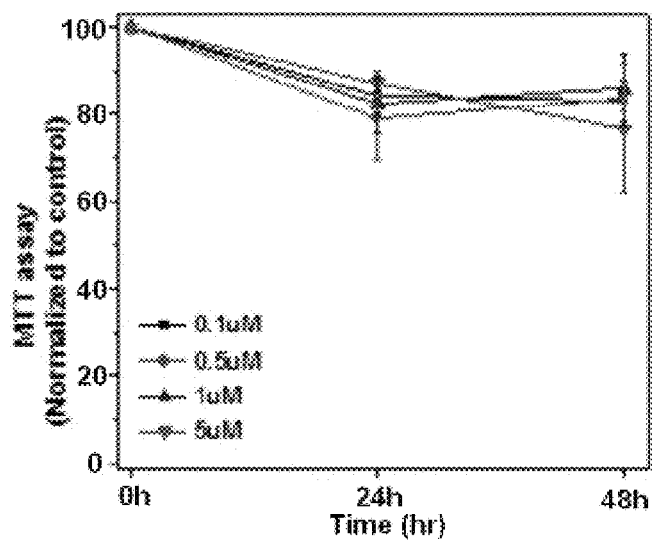
Figure 9D:
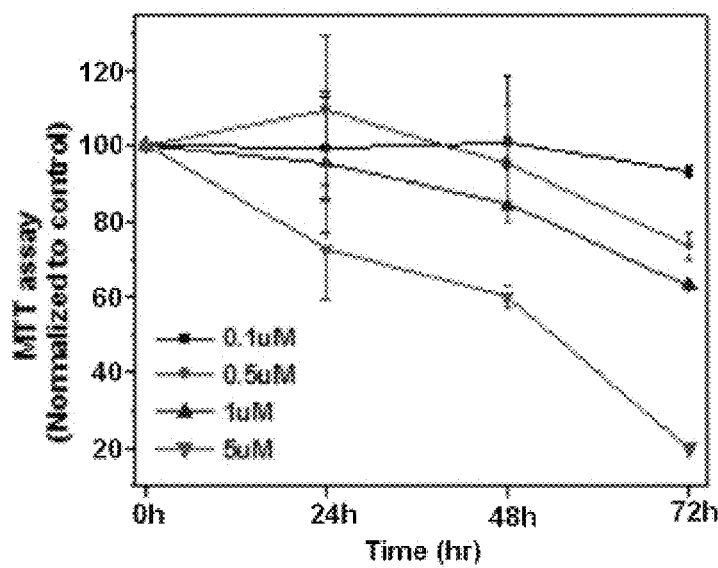
Figure 9E:
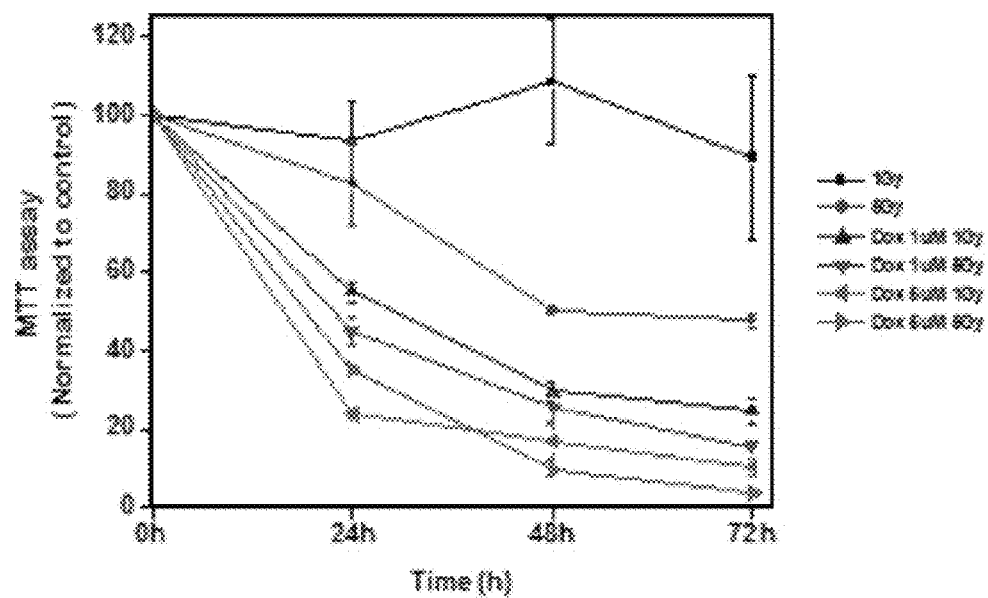
Figure 9F:
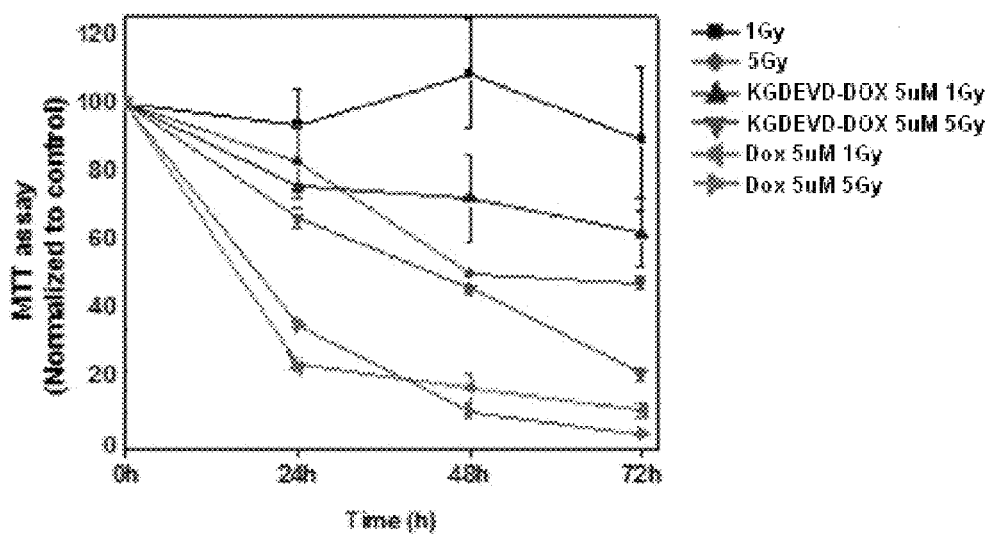

As shown in FIG. 8, when the anticancer prodrug according to the present Example was administered together with radiation of radioactive ray, tumor was reduced in size, similar to that in administration of doxorubicin with radiation.

EXAMPLE 4

Cytotoxicity Evaluation of Anticancer Prodrug

Cytotoxicity was evaluated by in vitro MTT assay.

In detail, SCC 7 cells were radiated at a dose of 1 Gy, 5 Gy, or 10 Gy, and then the medium was removed after 2 h, 6 h, 12 h, 24 h, or 48 h. 20 μl of MTT solution per 100 μl of medium was treated, and then reacted at 30° C. for 1 hour in the dark. Thereafter, the cells were washed with PBS three times, and the medium was removed. 100 μl of DMSO was added to dissolve MTT formazan, followed by ELASA (test wavelength: 570 nm).

That is, total 6 experiments were carried out, and the results are shown FIGS. 9a to 9f.

a) Radiation of cells at a radiation dose of 1 Gy, 5 Gy, 10 Gy, 15 Gy, 20 Gy, followed by MTT assay (radiation MTT assay), b) Treatment of cells with doxorubicin at a dose of 0.1 μM, 0.5 μM, 1 μM, and 5 μM, followed by MTT assay (Doxorubicin MIT assay), c) Treatment of cells with anticancer prodrug (KGDEVD-DOX) prepared in Example 1, followed by MTT assay (KGDEVD-DOX MTT assay), d) Treatment of cells with caspase-3-treated anticancer prodrug (KGDEVD-DOX) prepared in Example 1, followed by MIT assay (Cleaved Dox by Caspase-3 MIT assay), e) Treatment of cells with doxorubicin and radiation, followed by MIT assay (Doxorubicin+RT MTT assay), f) Treatment of cells with doxorubicin after anticancer prodrug (KGDEVD-DOX), followed by MTT assay (KGDEVD-DOX+RT MTT assay).

Figure 10A:
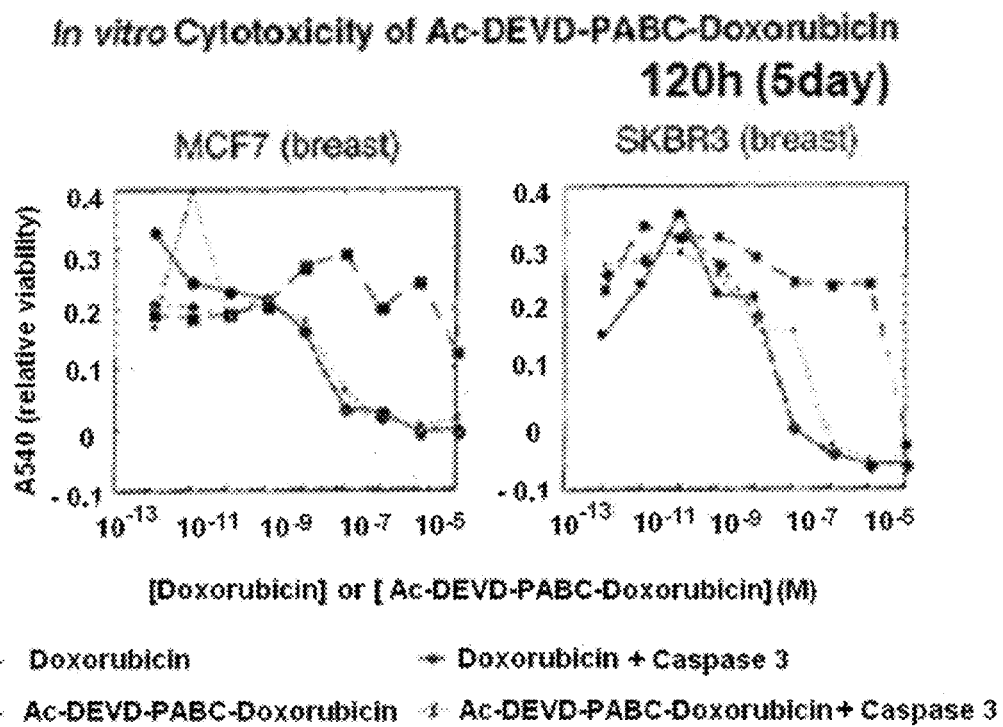

Further, as Comparative Example, AcDEVD-DOX disclosed in US Patent Publication No. 2007-0104719 (applicant: Genentech) was used to perform MTT assay by the above method, and the results are shown in FIGS. 10a and 10b.

Therefore, the anticancer prodrug (KGDEVD-DOX) prepared in Example 1 of the present invention showed more rapid and effective apoptotic effects on cancer cells than AcDEVD-DOX in Comparative Example, and showed no cytotoxicity when caspase-3 was not expressed.

EXAMPLE 5

In Vitro Cellular Uptake of Anticancer Prodrug

Cellular mechanism was imaged by in vitro cellular uptake study.

5.1. Treatment of Anticancer Prodrug (KGDEVD-Dox) of Example 1

SCC 7 cells were treated with KGDEVD-Dox prepared in Example 1. 3 h, 6 h, 12 h, 24 h, 48 h, and 72 h after treatment, the medium was removed, and the cells were washed with PBS three times, and fixed in a fixing solution. Cellular uptake images were obtained by fluorescence microscopy, and the results are shown in FIG. 12.

Further, SCC 7 cells were treated with KGDEVD-Dox of Example 1 at a dose of 5 μM. After 24 hr, the cells were radiated at a dose of 1 Gy, 5 Gy, or 10 Gy of radioactive ray. 3 hrs after radiation, the medium was removed, and the cells were washed with PBS three times, and fixed in a fixing solution. Cellular uptake images were obtained by fluorescence microscopy, and the results are shown in FIG. 14.

Thereafter, SCC 7 cells were treated with KGDEVD-Dox at a dose of 5 μM. After 24 hrs, the cells were radiated with UV (254 nm). 3 hrs after UV treatment, the medium was removed, and the cells were washed with PBS three times, and fixed in a fixing solution. Cellular uptake images were obtained by fluorescence microscopy, and the results are shown in FIG. 18.

Figure 18:
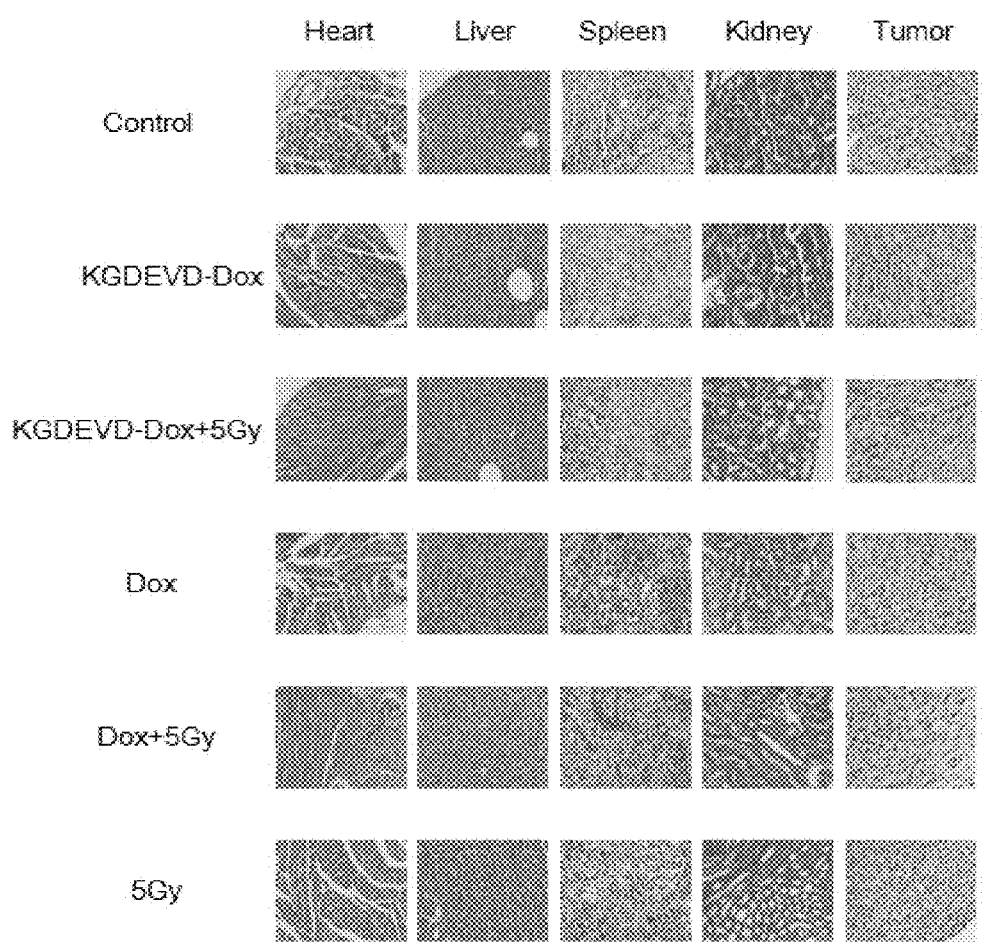
FIG. 18 shows cytotoxicity after treatment of a low dose of radiation and administration of a high dose of the anticancer prodrug according to the present invention.

FIGS. 12, 14, and 18 are images showing cellular uptake of KGDEVD-Dox of Example 1. In detail, FIG. 12 is the result of fluorescence microscopy of SCC 7 cells that were treated with KGDEVD-Dox of Example 1, but not treated with UV or radiation. FIG. 14 is a cellular uptake image after KGDEVD-Dox treatment and radiation. FIG. 18 is a cellular uptake image after KGDEVD-Dox treatment and radiation.

5.2. Comparative Observation

Figure 11:
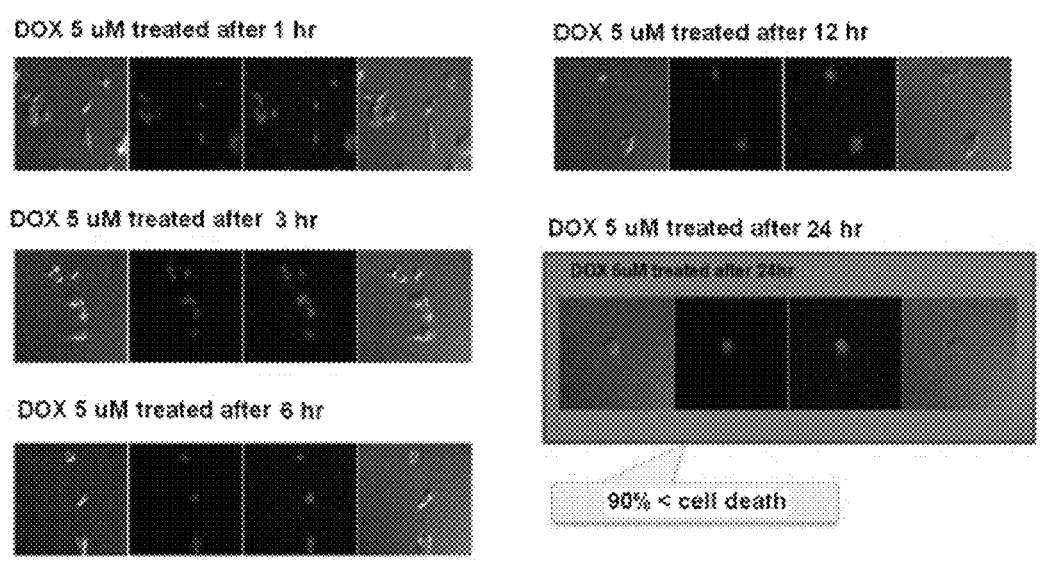
FIG. 11 is an image showing cellular uptake of doxorubicin.
Figure 13:
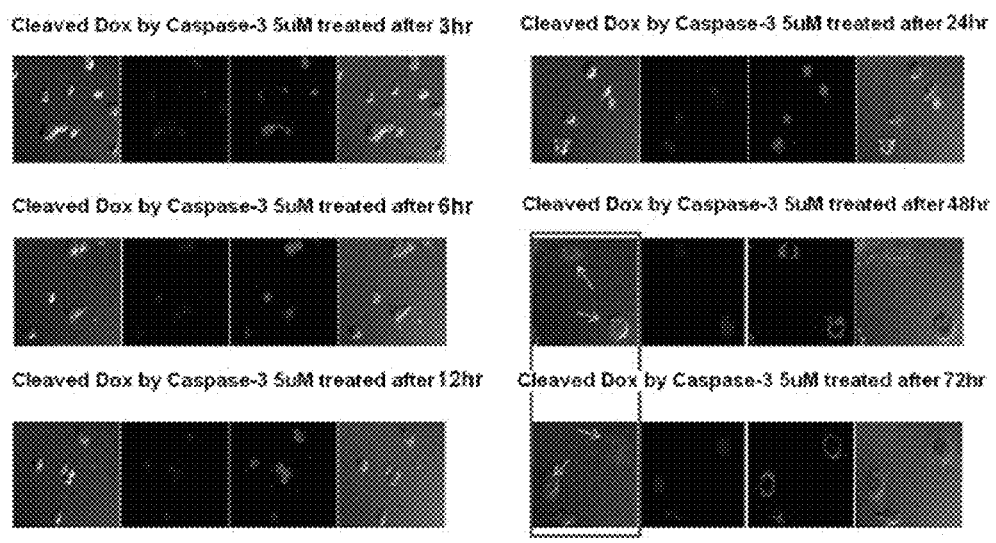
FIG. 13 is an image showing cellular uptake of the anticancer prodrug according to the present invention that is treated with caspase-3.
Figure 16:
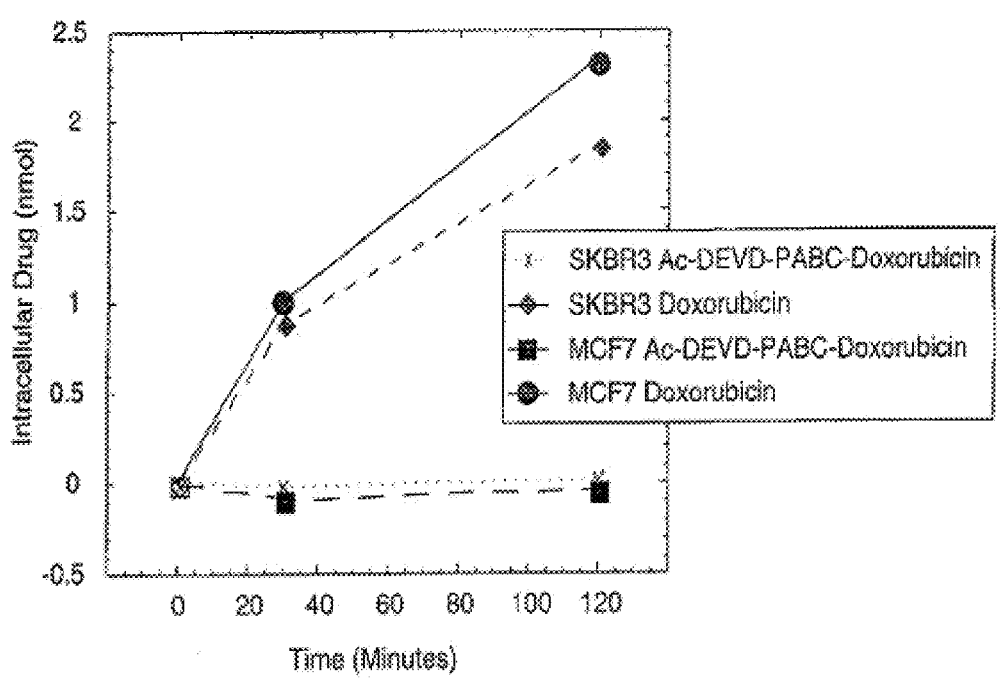
FIG. 16 is an image showing cellular uptake of the conventional AcDEVD-DOX that is disclosed in US Patent Publication No. 2007-0104719.

Observation results after doxorubicin treatment are shown in FIG. 11, observation results after doxorubicin and caspase-3 treatments are shown in FIG. 13, and fluorescence microscopic images of AcDEVD-PABC-DOX as Comparative Example are shown in FIG. 16. As shown in FIG. 16, no cellular uptake of AcDEVD-PABC-DOX was observed, but a cytosolic uptake of KGDEVD-Dox of the present invention was observed. When caspase-3 was expressed in cells by treatment of cells with caspase-3 or radiation, the linker of DEVD-Dox uptaken in the cytosol was cleaved into DEVD and Dox, and translocation of Dox into the nucleus was observed.

As shown in the images of FIGS. 11 to 14, and FIG. 15, KGDEVD-Dox before radiation of radioactive ray or UV is located not in the cytosol but in the nucleus. As caspase-3 is expressed after radiation of radioactive ray or UV, KGDEVD and doxorubicin are cleaved, and doxorubicin is translocated into the nucleus, which affects cancer cells.

EXAMPLE 6

Examination of Optimum Effect of Anticancer Prodrug

Based on the results of in vitro MTT assay and cellular uptake experiment previously performed, antitumor therapeutic effects and fewer side effects were examined by treatment of a high dose of anticancer prodrug and a low dose of radiation.

That is, tumor mouse models transplanted with SCC 7 cell line were radiated using a gamma knife (5 Gy). 24 hrs after radiation, the caspase-3 sensitive anticancer prodrug was administered into the animals via intravenous injection (10 mg/kg). At this time, the same dose of the drug was administered into the animals every day for 3 days, and then tumor growth and survival rate were measured every day until the experiments were terminated after radiation. The organs were removed from each experimental group after completion of the experiment, and cytotoxicity of the drug was examined.

Figure 17A:
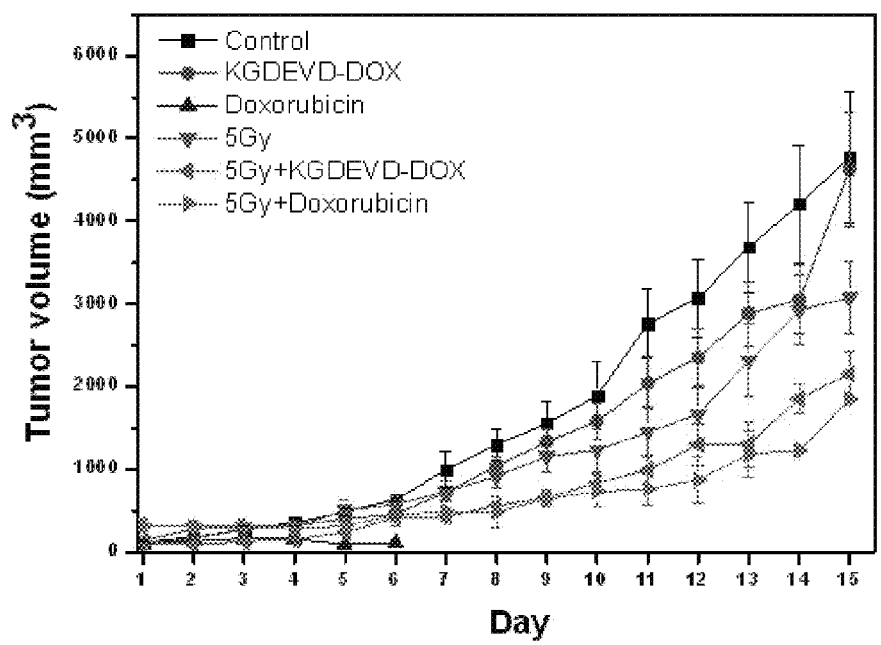
FIGS. 17a and 17b show anti-tumor therapeutic effect after treatment of a low dose of radiation and administration of a high dose of the anticancer prodrug according to the present invention.
Figure 17B:
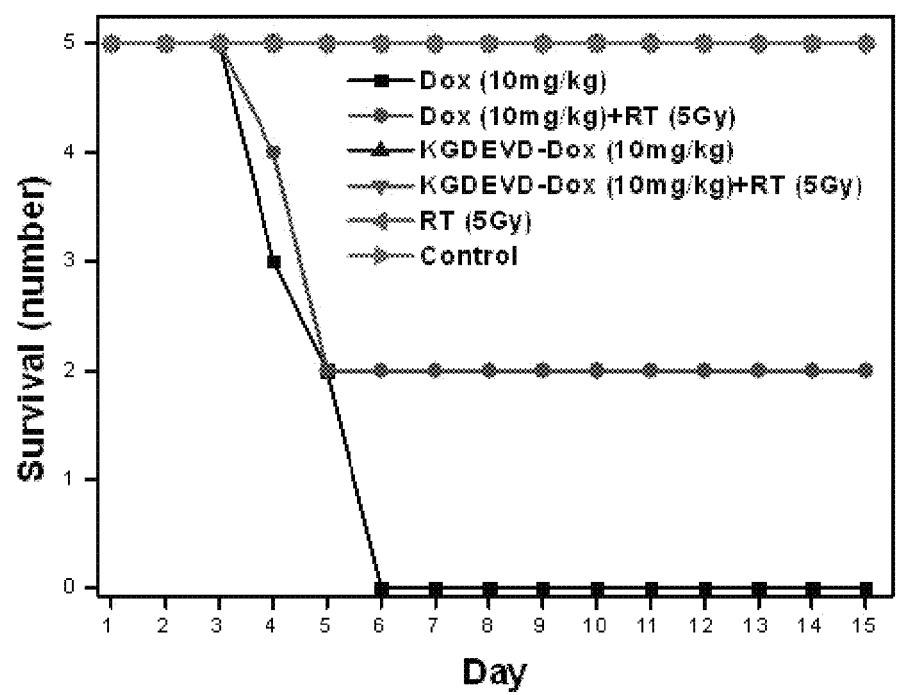

As shown in FIGS. 17a, 17b and 18, it was found that treatment of a low dose of radiation and a high dose of anticancer prodrug increased the antitumor therapeutic effect of the drug, but reduced side effects.

Taken together, the present inventors developed tumor-recognizing and apoptosis-sensitive nanoparticles capable of selectively targeting tumors by radiation, which is a novel progressive drug for effectively killing cancer cells while minimizing side effects in the body caused by the conventional radiotherapy and anticancer drug. In particular, cellular uptake of the active ingredient into tumor cells is higher than the conventional technology, and no cytotoxicity was observed when no caspase-3 is expressed.

Effect of the Invention

According to the anticancer prodrug of the present invention, an anticancer drug unstable in acid or base such as doxorubicin is effectively provided in a form of prodrug. Thus, the anticancer prodrug exists as an inactive form when administered into the body, but effectively releases the anticancer drug as an active ingredient in the target area in the presence of caspase activated by radiation or UV treatment after administered into the body. Accordingly, the anticancer drug exhibits selective anticancer effects on cancer cells, thereby maximizing the therapeutic effect and minimizing the side-effects of radiation or UV treatment.

What is claimed is:

1. An anticancer therapeutic kit, comprising:
a prodrug comprising (i) a peptide consisting of acetyl-SEQ ID NO: 1, (ii) a linker, and (iii) an anticancer drug that are sequentially linked to each other, wherein the linker is selected from the group consisting of para-aminobenzyloxycarbonyl, aminoethyl-N-methylcarbonyl, a dendritic linker and a cephalosporin-based linker; and
an apparatus for applying radiation to a subject at a dose between 1 Gy to 5 Gy or UV radiation at a dose between 1 J/m$^2$ to 50 J/m$^2$ UV so as to induce caspase activation in tumor cells in the subject.

2. The anticancer therapeutic kit of claim 1, wherein the anticancer drug is selected from the group consisting of doxorubicin, paclitaxel, adriamycin, cisplatin, 5-fluorouracil, mitomycin, chlomomycin, bleomycin, peplomycin, daunorubicin, aclarrubicin, neocarzinostatin, epirubicin, idarubicin and pirarubicin.

3. The anticancer therapeutic kit of claim 1, wherein the anticancer drug is doxorubicin, and the linker is para-aminobenzyloxycarbonyl.

4. The anticancer therapeutic kit according to claim 1, wherein the apparatus is for radiation treatment at a dose of 1Gy to 5Gy.

5. The anticancer therapeutic kit according to claim 1, wherein the apparatus is for UV radiation at a dose between 1 J/m$^2$ to 50 J/m$^2$ UV.

6. The anticancer therapeutic kit according to claim 1, wherein the linker is selected from the group consisting of para-aminobenzyloxycarbonyl, aminoethyl-N-methylcarbonyl, aminobiphenylmethyloxycarbonyl, a dendritic linker and a cephalosporin-based linker.

7. The anticancer therapeutic kit according to claim 1, wherein the linker is para-aminobenzyloxycarbonyl.

* * * * *

SEQUENCE LISTING

```
<160> NUMBER OF SEQ ID NOS: 1

<210> SEQ ID NO 1
<211> LENGTH: 6
<212> TYPE: PRT
<213> ORGANISM: Homo sapiens
<220> FEATURE:
<221> NAME/KEY: MOD_RES
<222> LOCATION: (1)
<223> OTHER INFORMATION: ACETYLATOIN,

<400> SEQUENCE: 1

Lys Gly Asp Glu Val Asp
1               5
```